(12) United States Patent
Blake, III

(10) Patent No.: US 10,939,918 B2
(45) Date of Patent: *Mar. 9, 2021

(54) MULTI-CLIP APPLIER

(71) Applicant: Joseph W. Blake, III, New Canaan, CT (US)

(72) Inventor: Joseph W. Blake, III, New Canaan, CT (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/972,155

(22) Filed: May 6, 2018

(65) Prior Publication Data

US 2018/0250012 A1 Sep. 6, 2018

Related U.S. Application Data

(63) Continuation of application No. 14/883,694, filed on Oct. 15, 2015, now Pat. No. 9,968,363.

(60) Provisional application No. 62/122,406, filed on Oct. 20, 2014.

(51) Int. Cl.
*A61B 17/128* (2006.01)

(52) U.S. Cl.
CPC .............................. *A61B 17/1285* (2013.01)

(58) Field of Classification Search
CPC ..... A61B 17/10; A61B 17/105; A61B 17/128; A61B 17/1285; A61B 17/0487; A61B 17/08; A61B 17/083; A61B 17/085; A61B 17/122; A61B 17/1222; A61B 34/71; A61B 2034/715; A61B 2017/0488; A61B 2017/088; A61B 2017/081; A61B 2017/1225

See application file for complete search history.

(56) References Cited

U.S. PATENT DOCUMENTS 9,968,363 B2 * 5/2018 Blake, III .......... A61B 17/1285

* cited by examiner

*Primary Examiner* — Kathleen S Holwerda
*Assistant Examiner* — Brooke Labranche
(74) *Attorney, Agent, or Firm* — Neil D. Gershon

(57) ABSTRACT

A clip applier having a handle at a proximal portion, an elongated portion extending distally of the handle, a jaw mechanism including a pair of jaws movable to a closed position to crimp a clip held therein, a clip feeder mechanism movable in proximal and distal directions, a camming mechanism and a puller mechanism movable in proximal and distal directions. The puller mechanism is operatively connected to the handle such that actuation of the handle a) moves the puller mechanism a first distance in the proximal direction; and b) moves the clip feeder mechanism a second distance greater than the first distance.

3 Claims, 41 Drawing Sheets

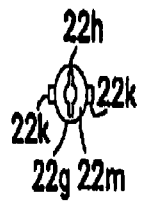
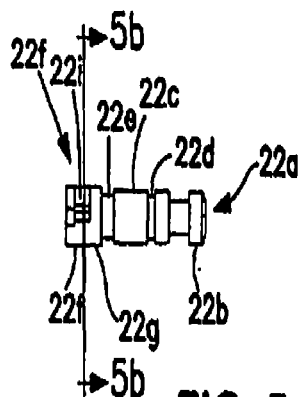
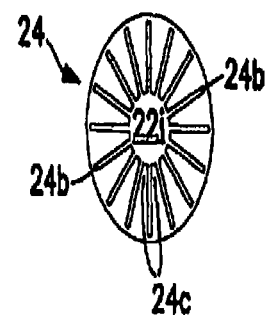
FIG. 5b  FIG. 5c  FIG. 5a  FIG. 7
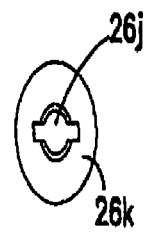
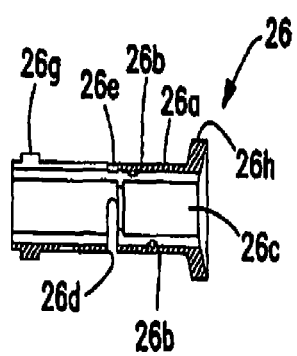
FIG. 6d  FIG. 6b
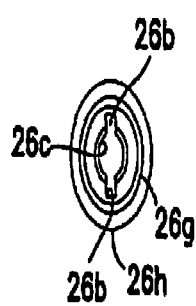
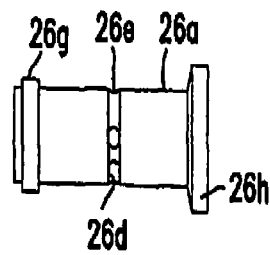
FIG. 6c  FIG. 6a

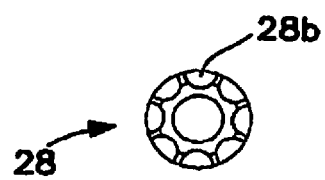 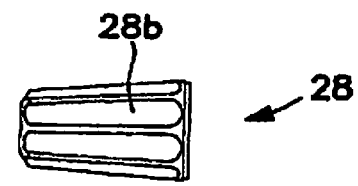
FIG. 8c    FIG. 8a
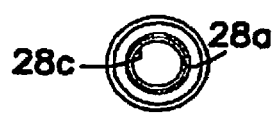 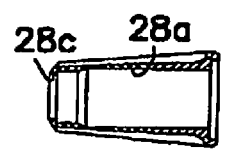
FIG. 8d    FIG. 8b

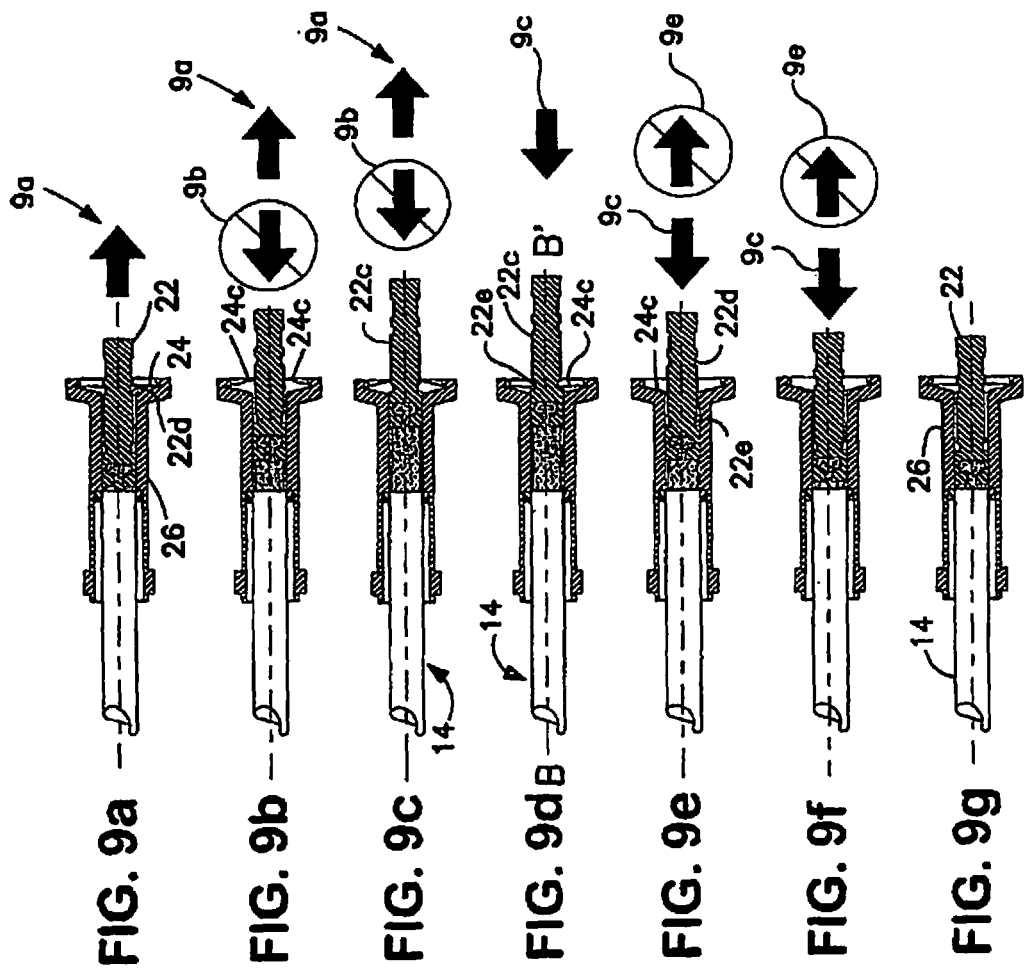

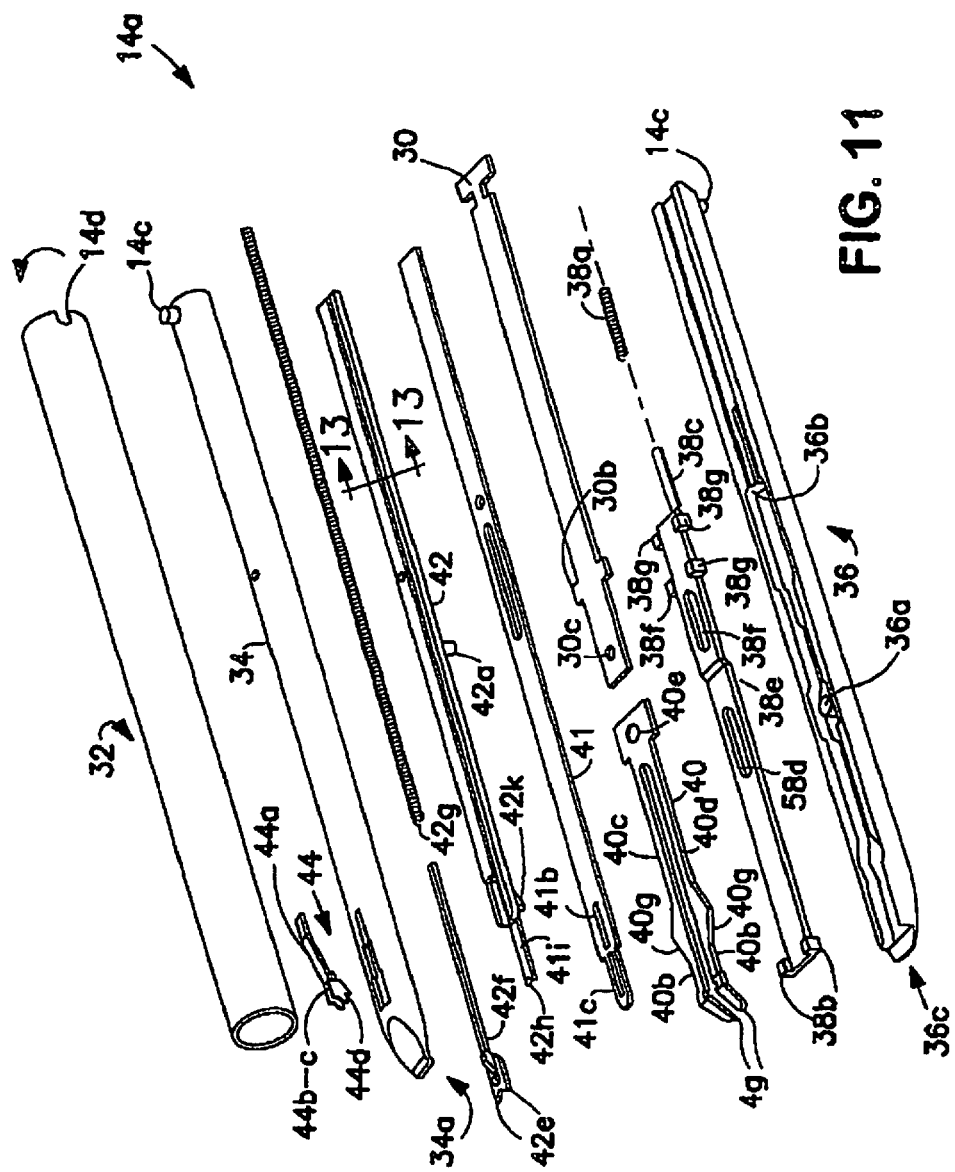

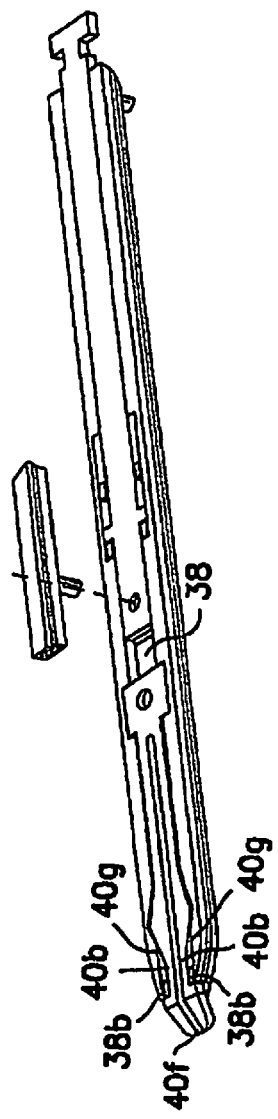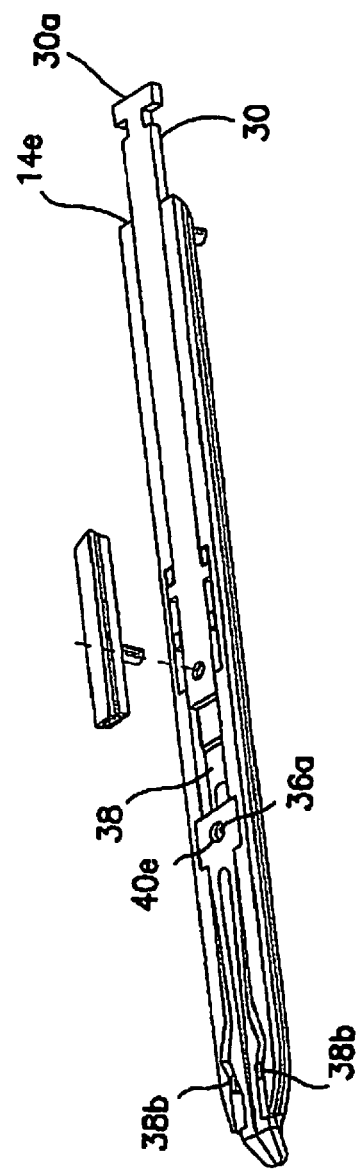

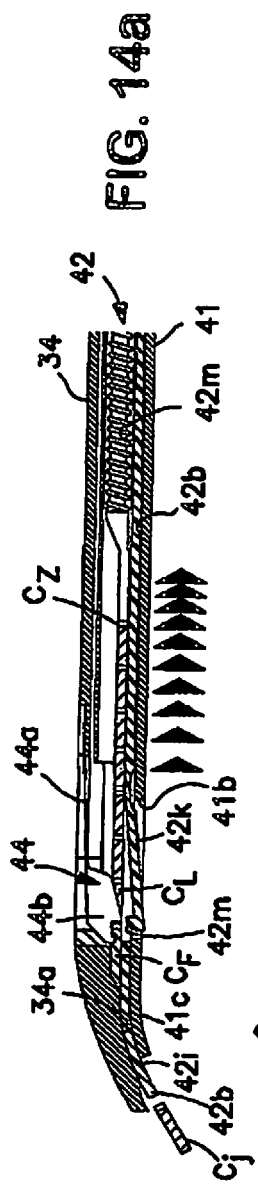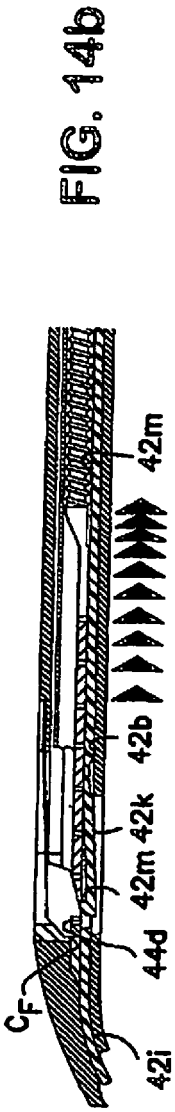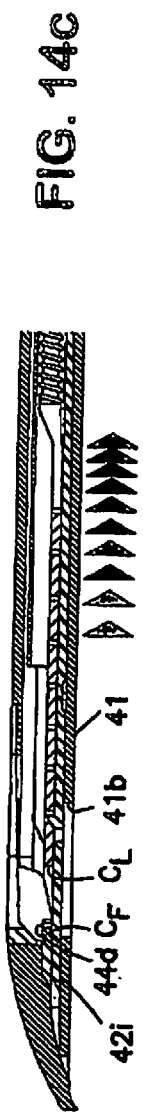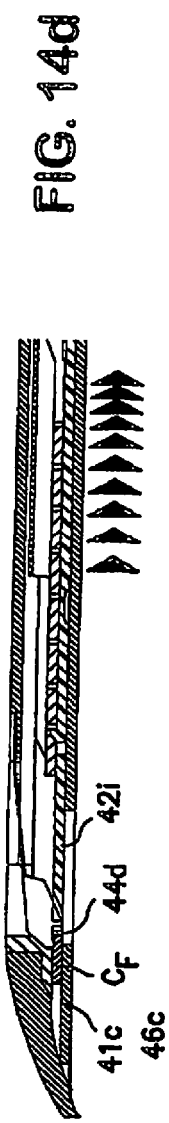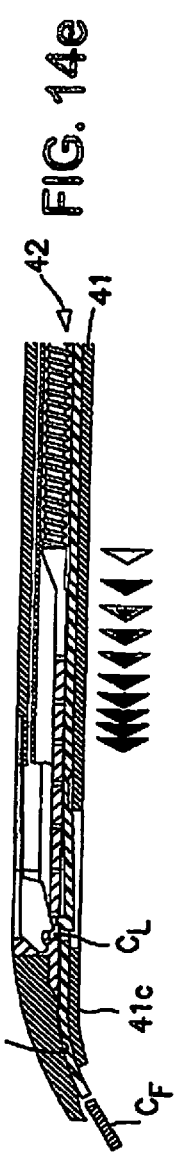
FIG. 14a
FIG. 14b
FIG. 14c
FIG. 14d
FIG. 14e

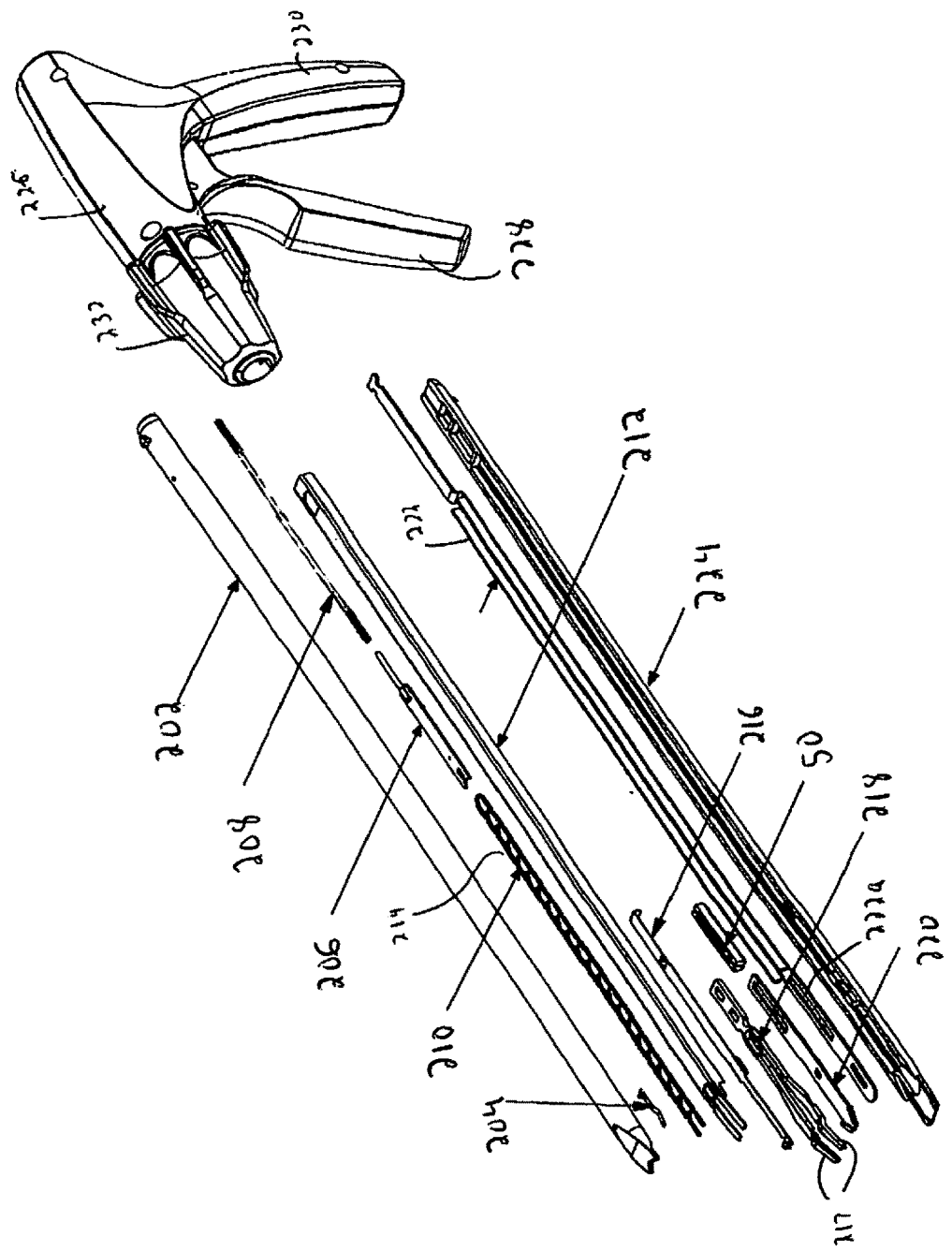

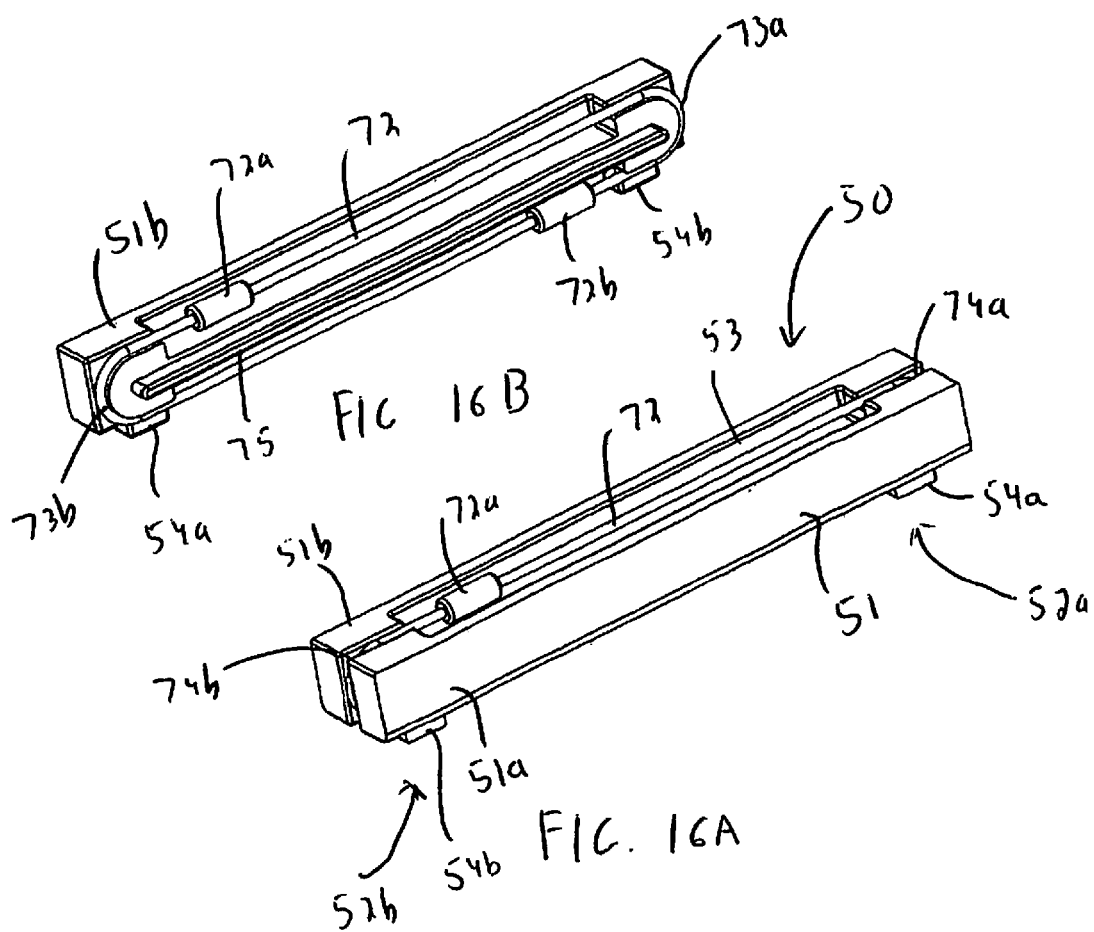

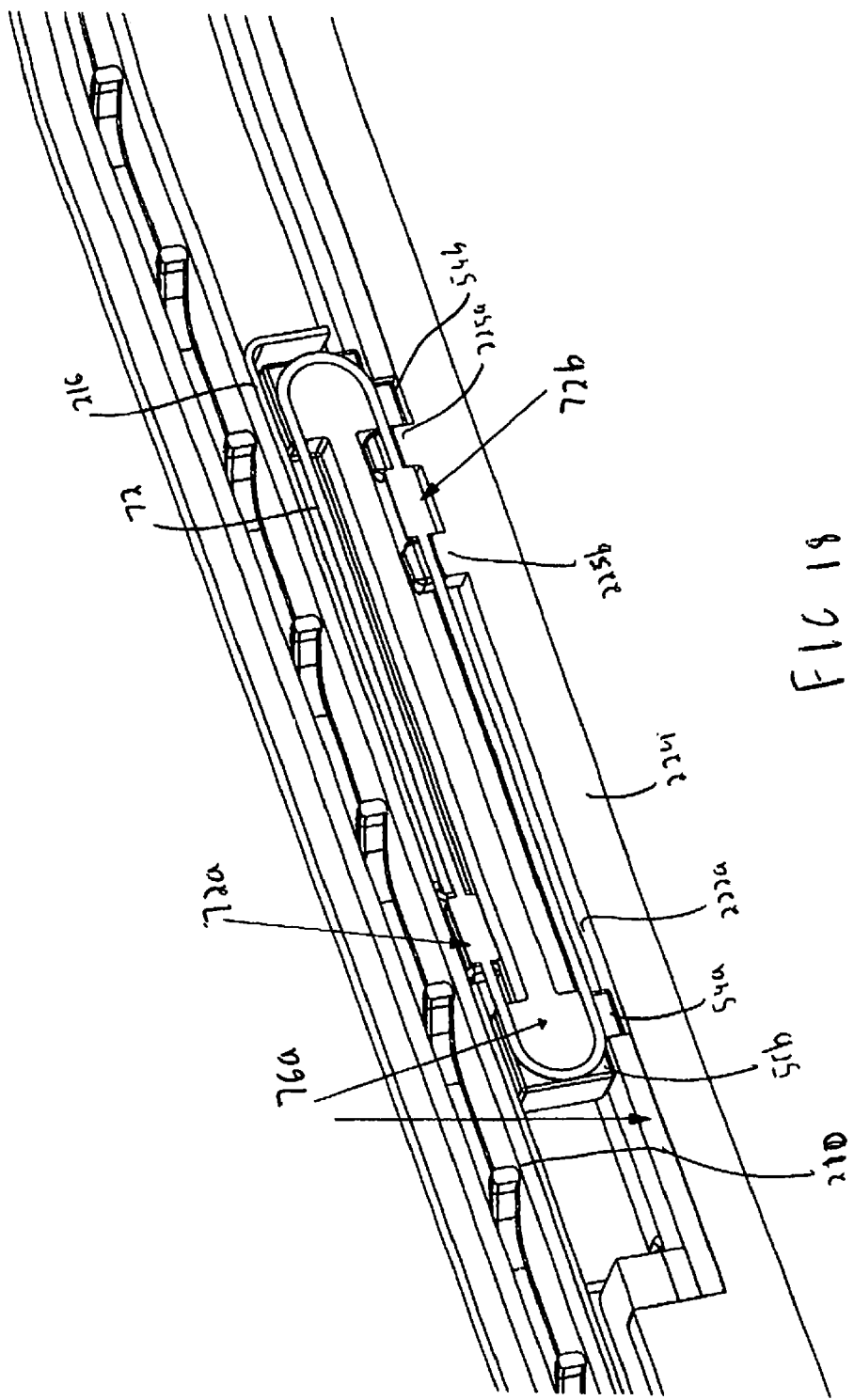

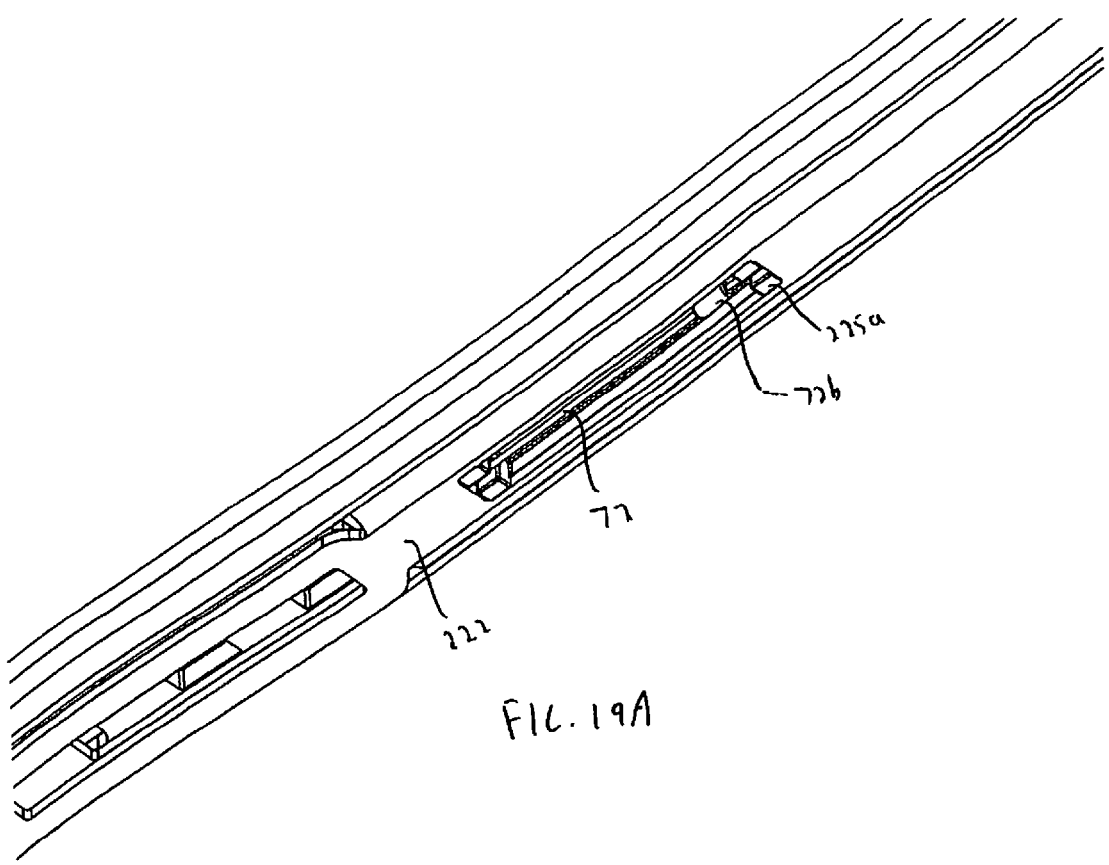

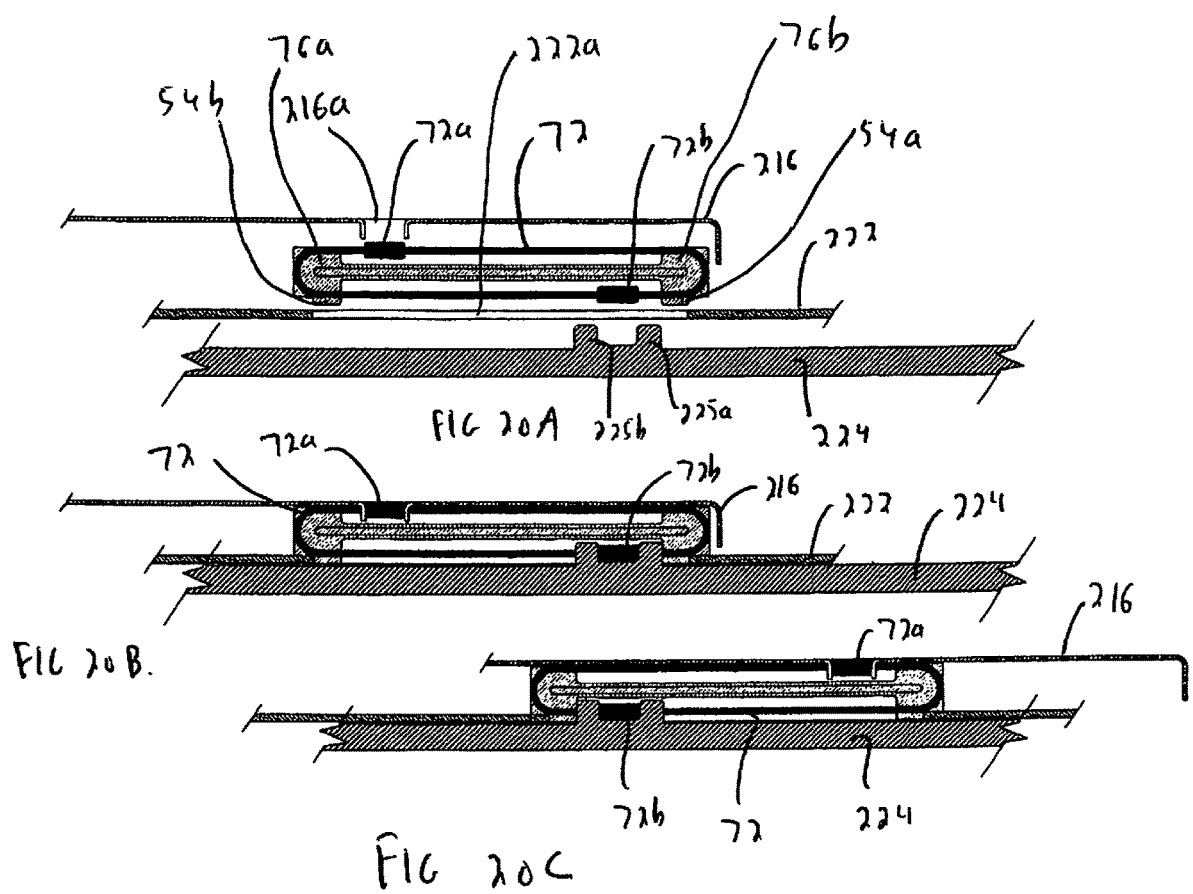

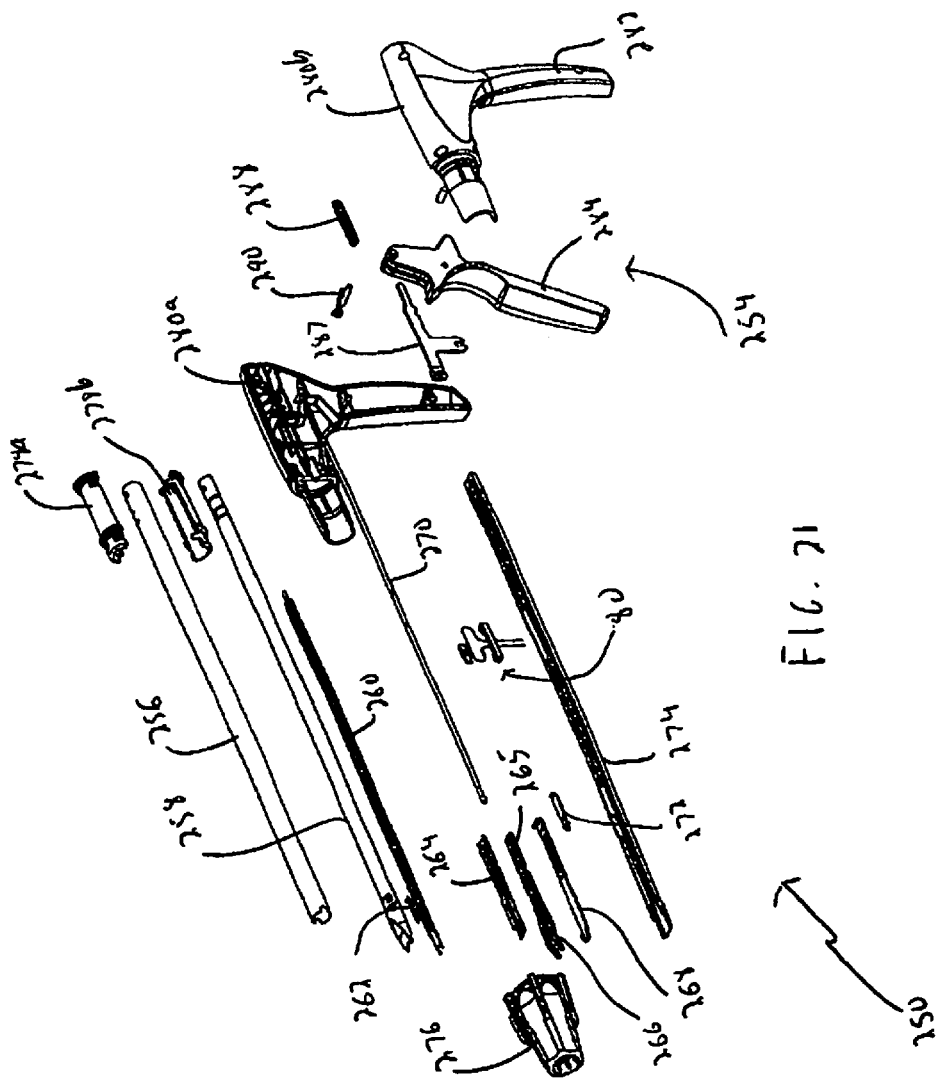

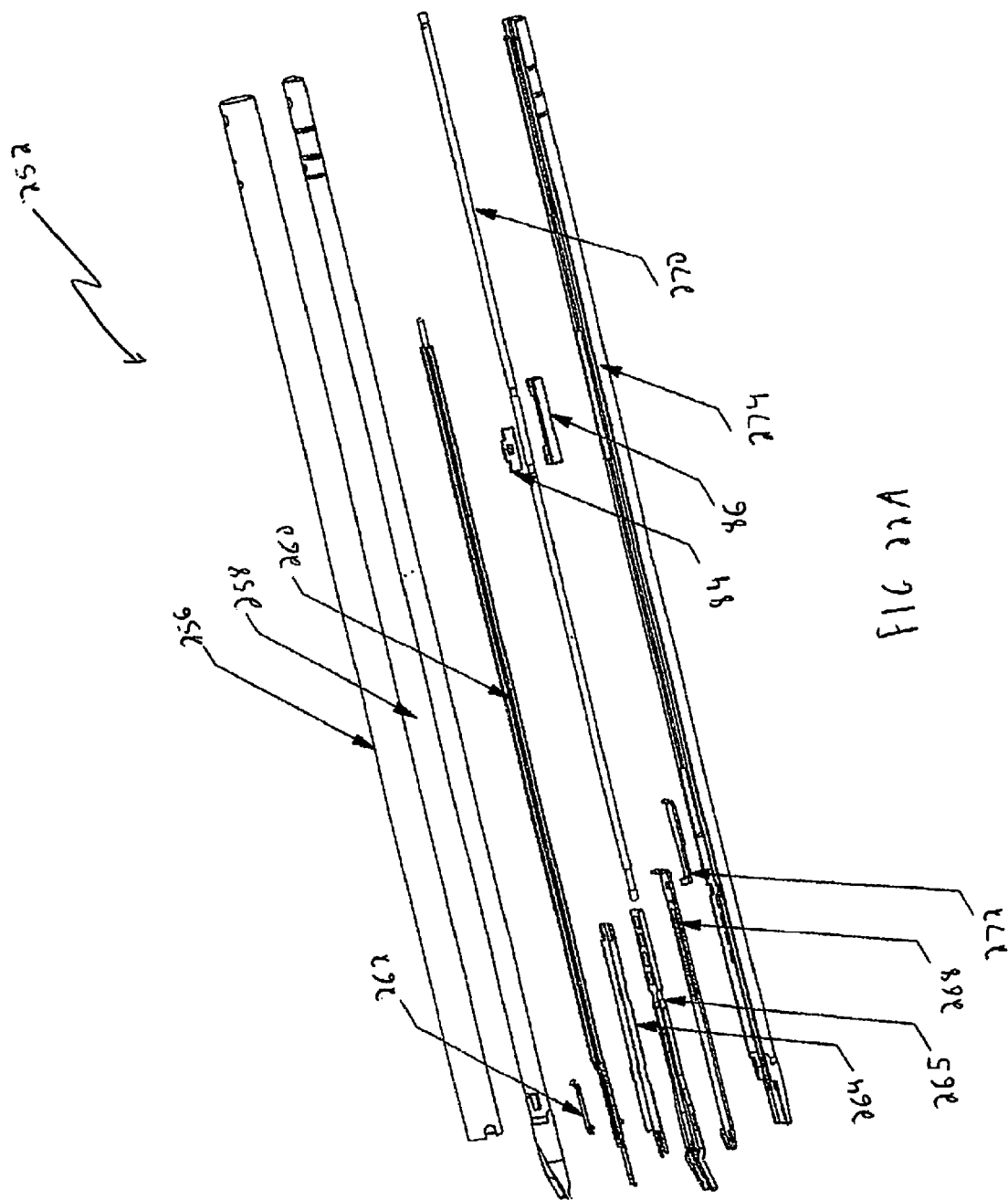

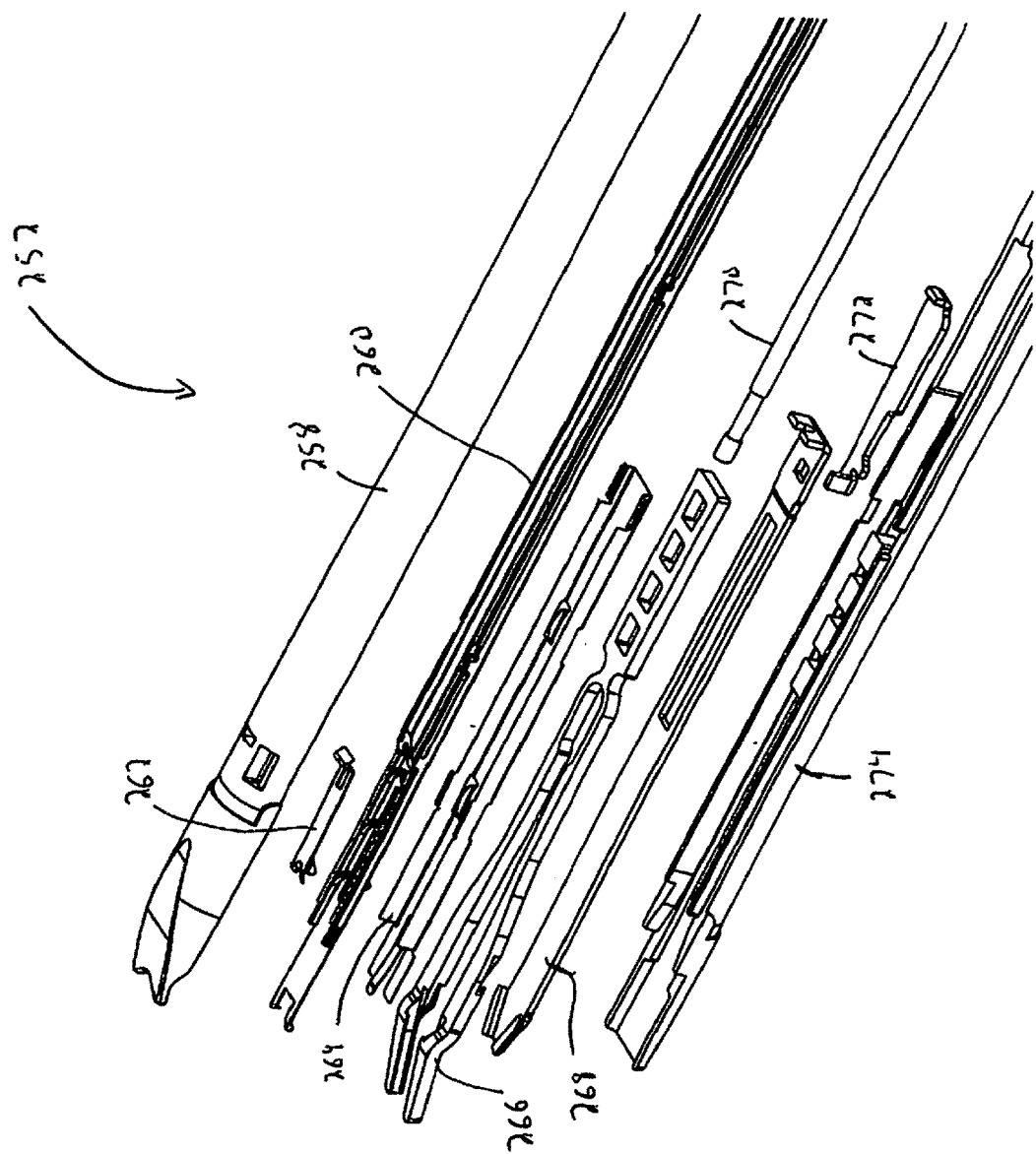

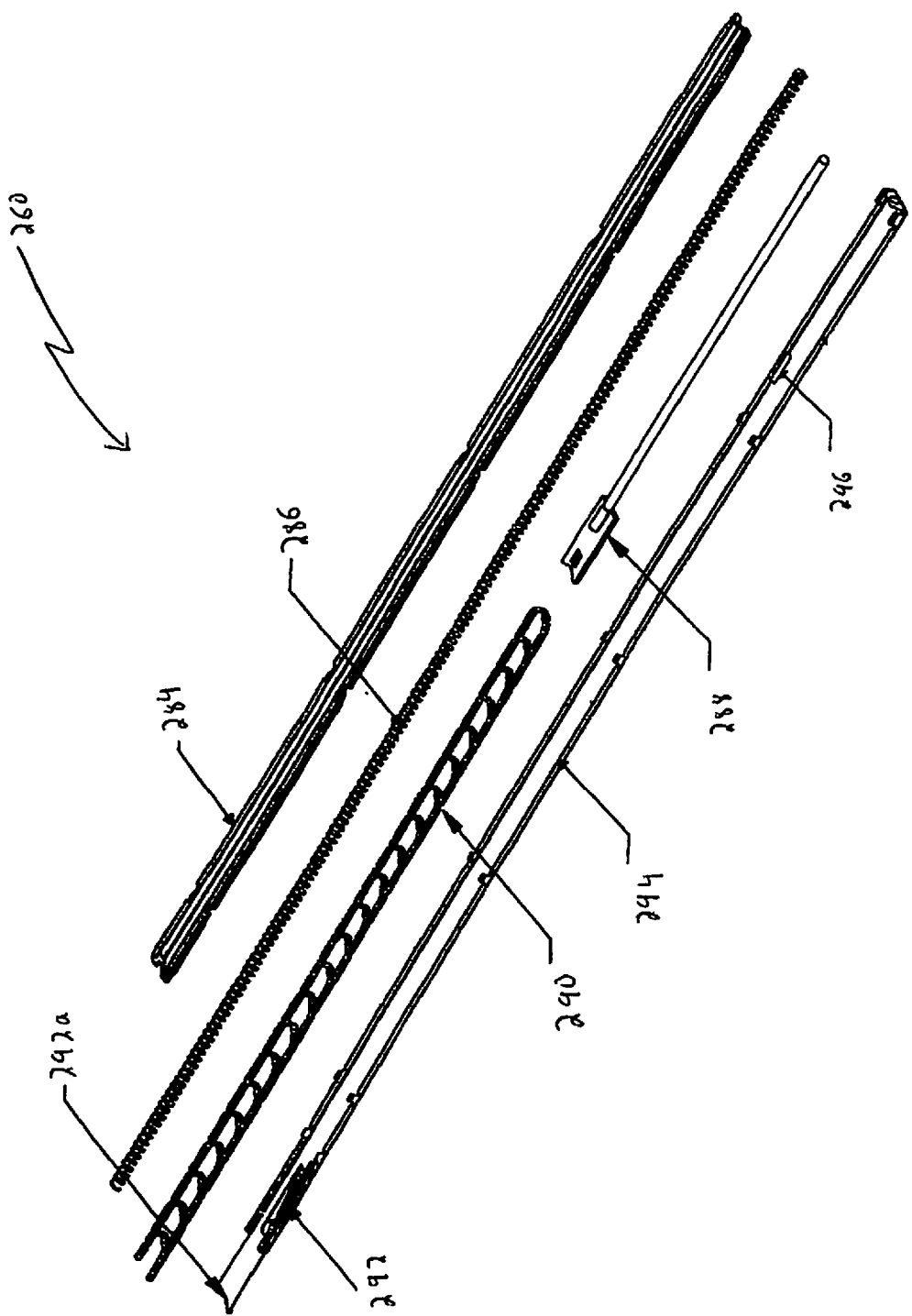

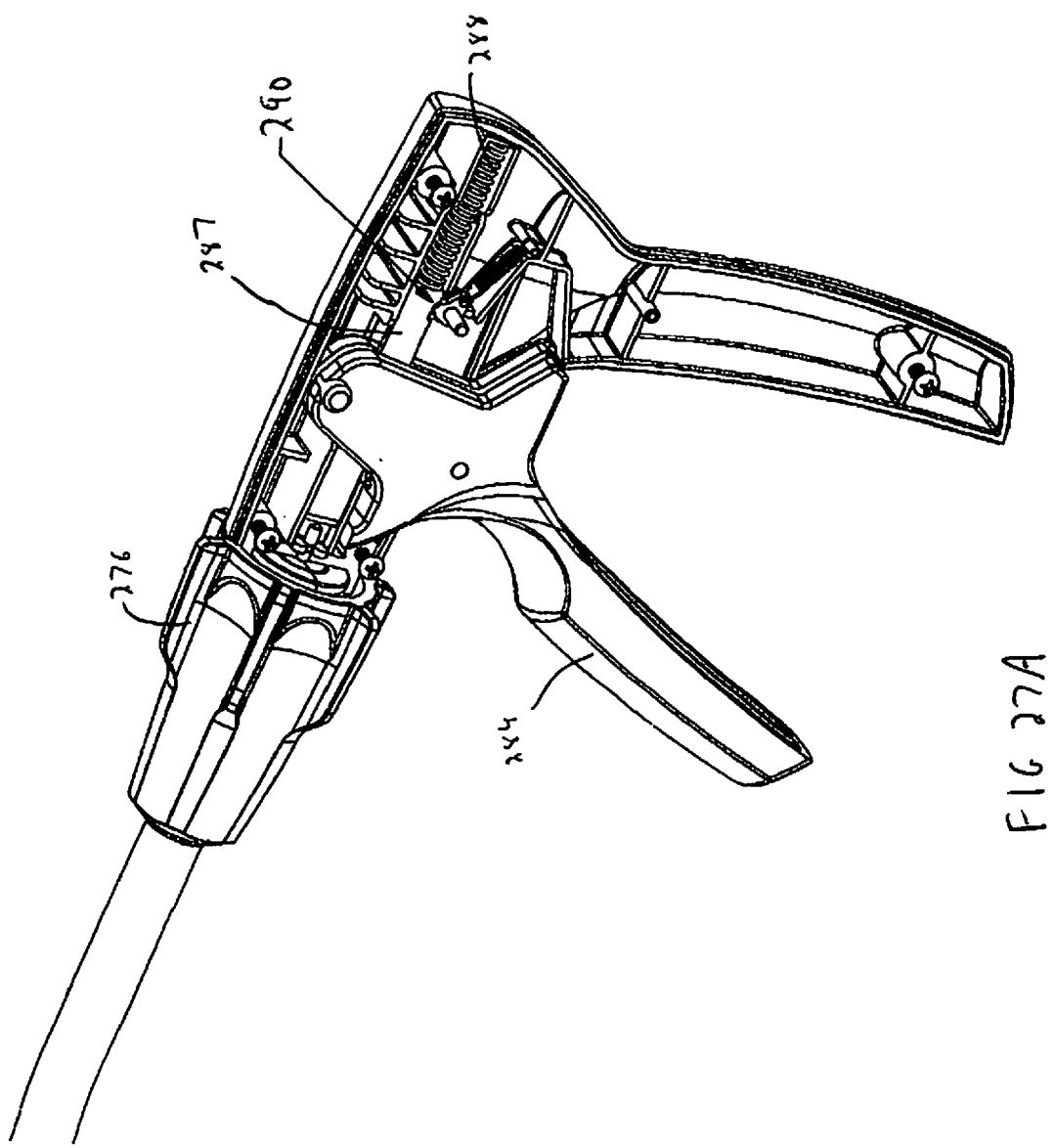

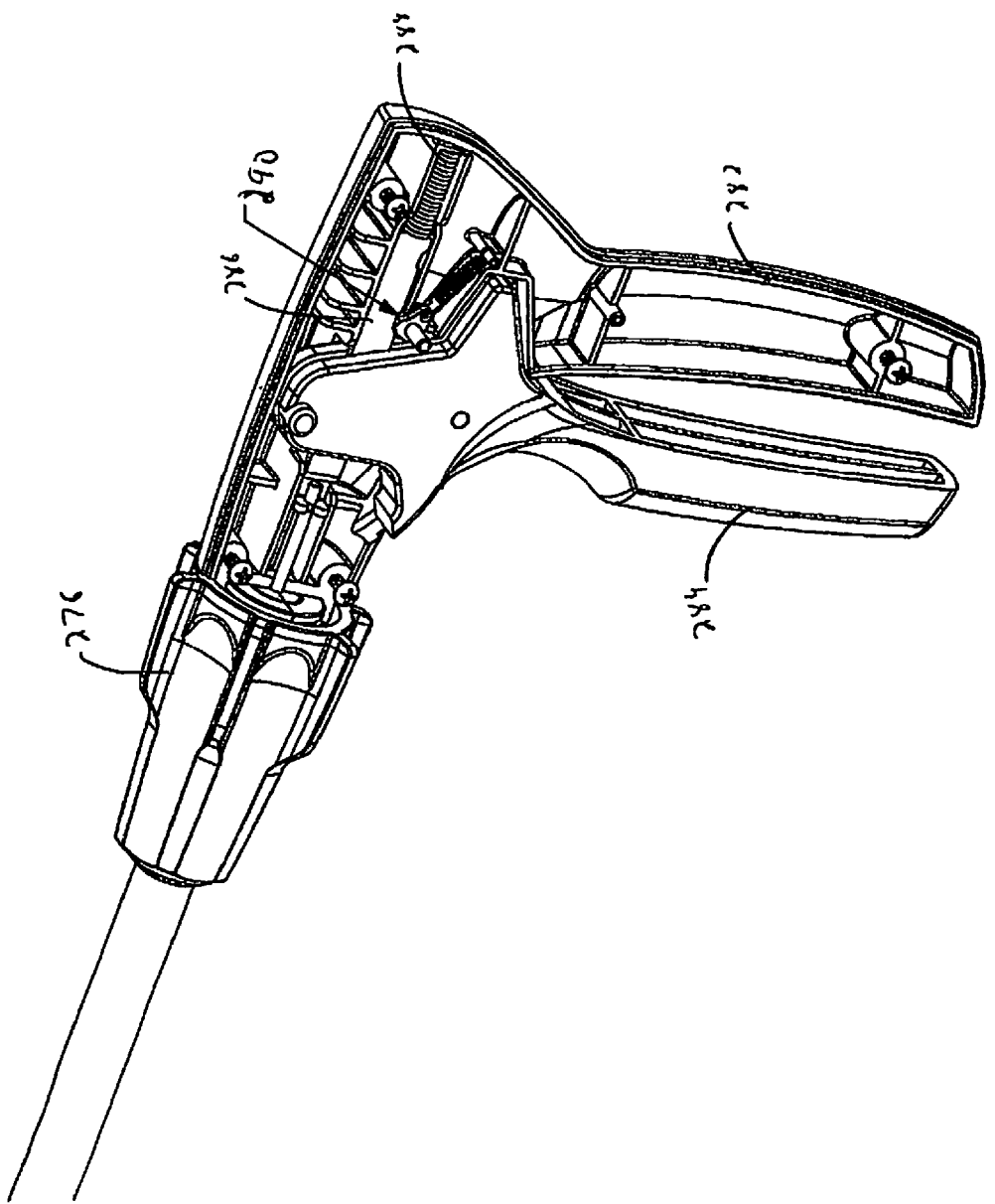

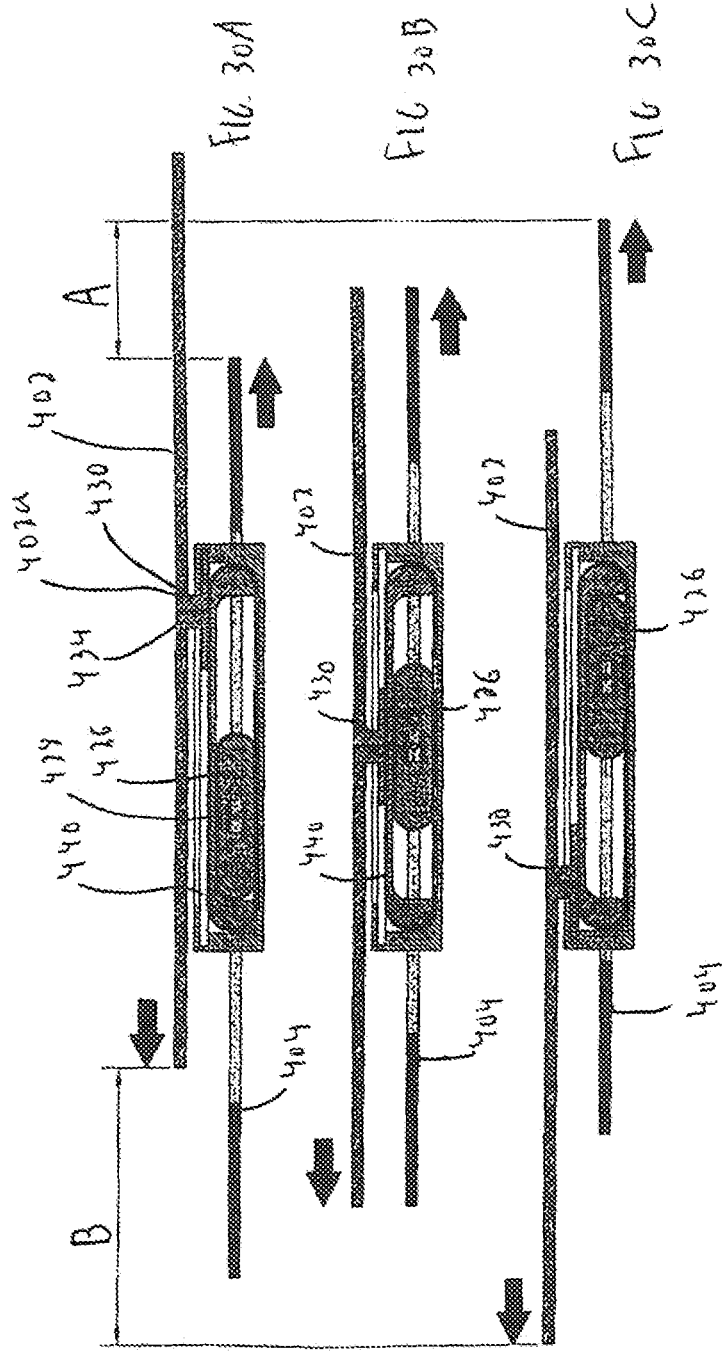

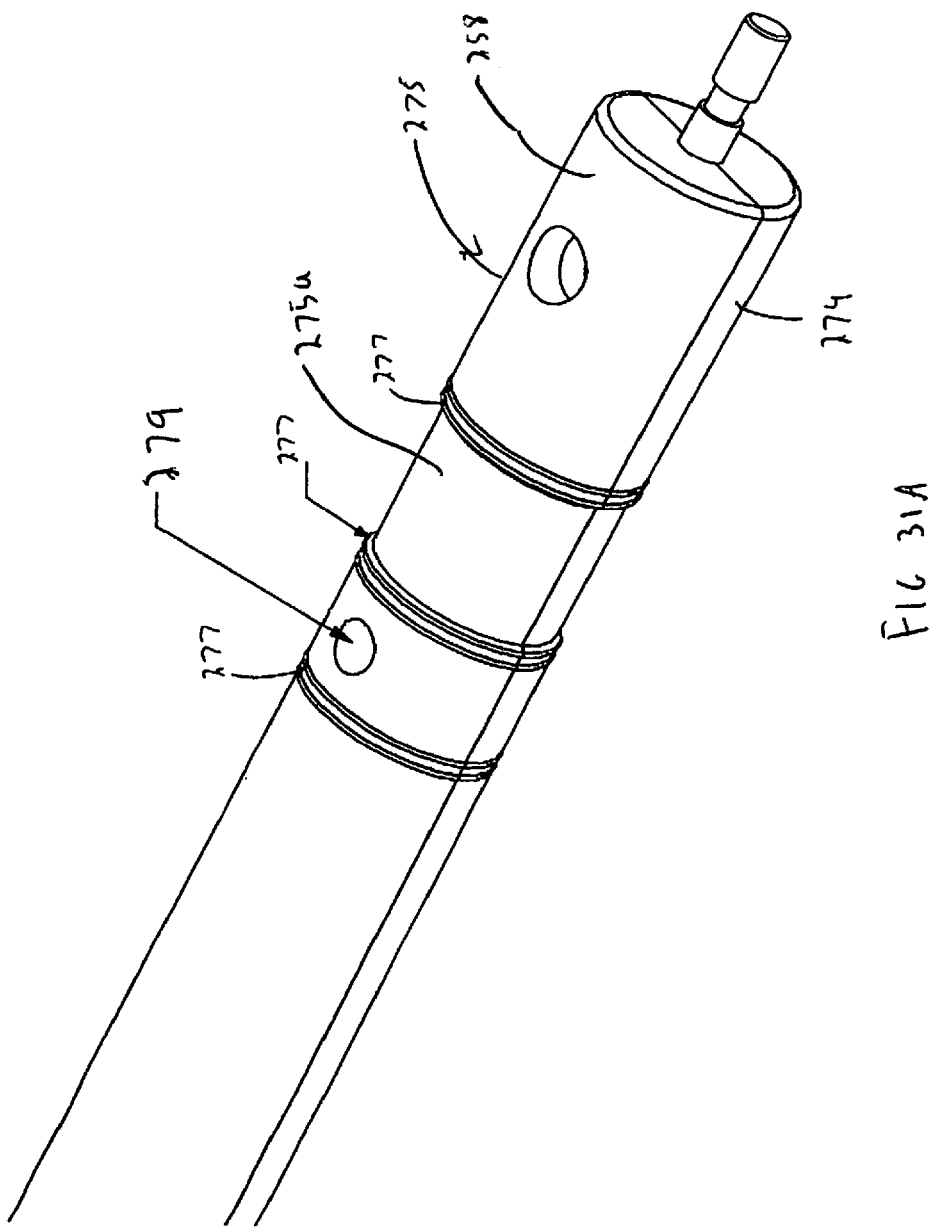

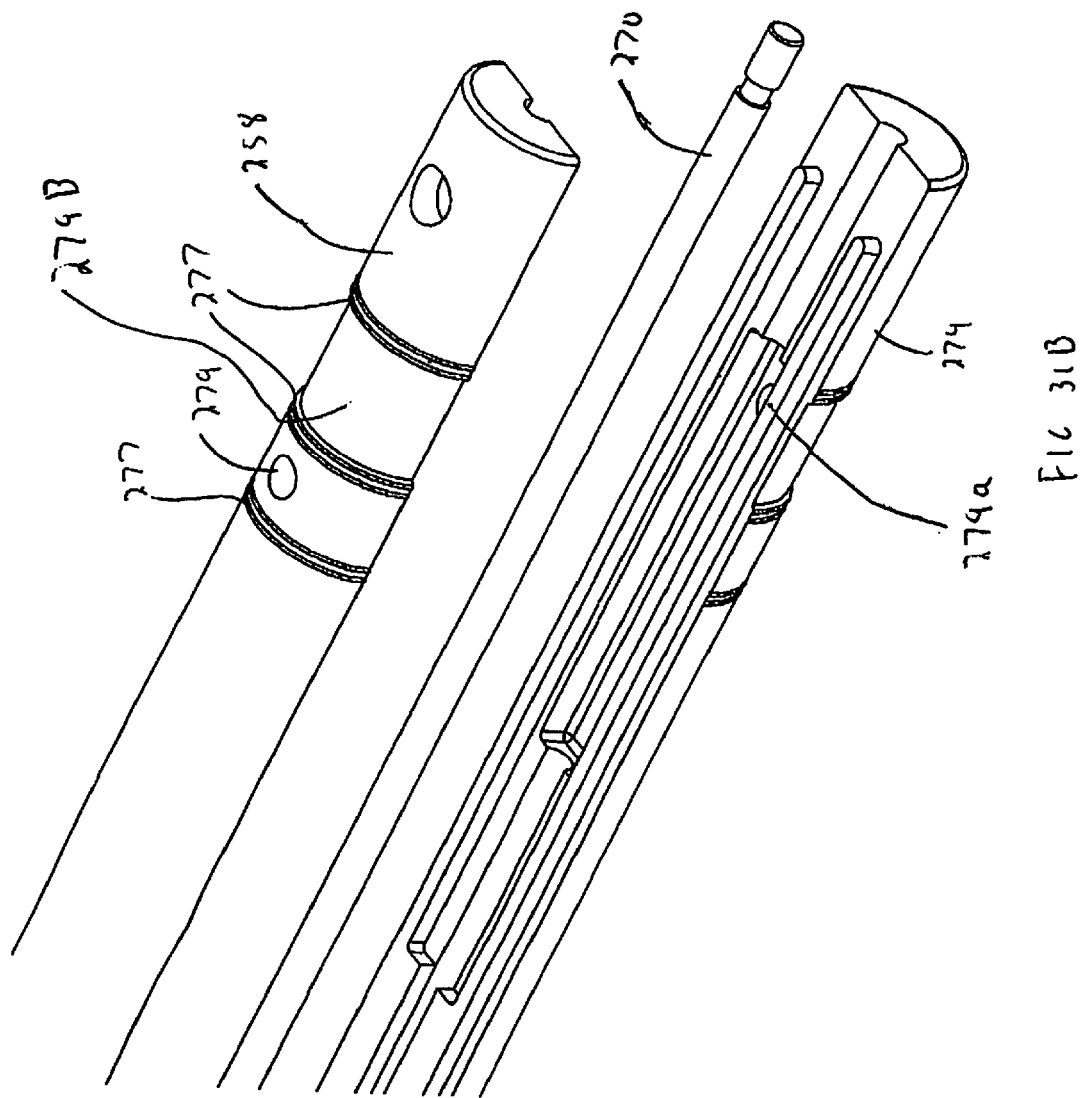

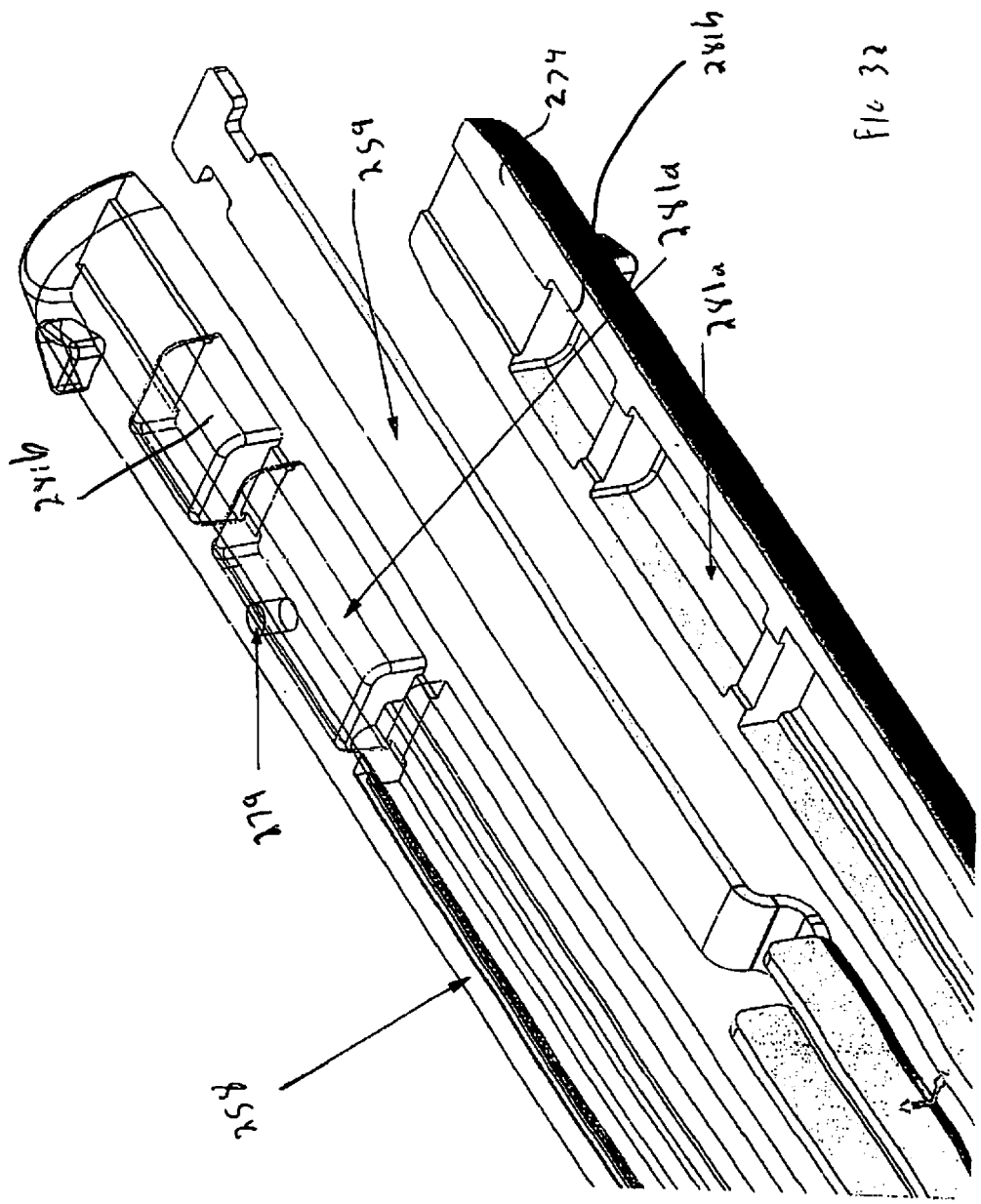

MULTI-CLIP APPLIER

This application is a continuation of application Ser. No. 14/883,694, filed Oct. 15, 2015, which claims the benefit of provisional application Ser. No. 62/122,406, filed Oct. 20, 2014. The entire contents of each of these applications are incorporated herein by reference.

BACKGROUND OF THE INVENTION

Technical Field

The present invention relates to surgical clip appliers embodied as an instrument having a supply of clips for rapidly deploying several clips in closing severed blood vessels and other small fluid carrying ducts in surgical procedures.

Background of Related Art

There are many different designs for surgical clip applicators for a variety of surgical procedures including both open surgery and laparoscopy in which a clip applier fits through a trocar tube into a body cavity where the clips are applied.

Current surgical clip appliers include an operating handle and a clip applying mechanism having an operating cycle in which jaws are squeezed together to apply a clip and released. In this operating cycle, a clip is applied to tissue in surgery and the clip applier is reloaded with a single clip from a clip supply channel for clip application in the next cycle. The applicator provides a moveable clip supply channel containing a line of clips that are released seriatim.

In U.S. Pat. Nos. 6,869,435 and 6,423,079, clip crimping jaws apply a clip with a rearward movement of a camming member thereby allowing the functions of clip loading and jaw closure to be coordinated and operated by a single sliding bar moving reciprocally to load and fire clips. The supply channel containing the line of clips integrates a clip pusher and an escapement or clip stop spring in a single unit. The clip actuating mechanism includes a combined actuating rod and in-line clip supply channel together with clip indexing mechanisms arranged so that with a squeeze of the operating levers, the actuating rod moves rearward in the appliance to apply a clip in surgery, capture the next in-line clip, index a line of clips rearward away from the clip jaws; and that with release of the operating levers, the jaws open, the next in-line clip is loaded into the jaws, the second next in-line clip is separated from the line, and the clip indexing movement is reset for the next cycle. The clip applicator includes a mechanism with minimal complexity especially suited for a disposable cartridge for fixed handle appliances. The clip applicator of the '079 patent also employs low operating force without recoil, a clip counter, jaw lockout after the last clip and is adaptable for use as a quick snap-in disposable cartridge with a fixed non-disposable operating handle. An operating handle that provides linear reciprocating motion including scissors-type or pistol grip is used with that invention.

In practice, clip cartridges are ordinarily used a single time and discarded. Operating handles, on the other hand, may be disposed of after use with a single cartridge, may be used with a plurality of cartridges in a single surgical procedure and then discarded, or may be autoclaved after each surgical procedure and used over and over again.

This invention in U.S. Pat. No. 6,689,435 provided improvements for a repeating multi-clip applier having a simplified mechanism for applying clips which mechanism was suitable for the full spectrum of clip appliers including open surgery and laparoscopy. The applier mechanism was particularly adaptable to the disposable cartridge/fixed handle design. The simplified mechanism reduced tooling and assembly requirements, providing high operating reliability at lower product cost.

The handle stroke for applying clips differs with different clip sizes, i.e., a longer clip requires a longer stroke, This means that a different handle needs to be utilized with different size clips. For example, a longer clip requires a longer stroke. It would be advantageous to provide a single handle with a consistent stroke to accommodate different size clips. This would provide manufacturing advantages since a single handle design can then be utilized for different size clips. It would also have the advantage in clip appliers with disposable cartridges since cartridges containing different size clips could be loaded onto the same handle. This consistent stroke universal handle would have application to both open and laparoscopic clip appliers.

Additionally, with the growth of minimally invasive surgery, there is a need for smaller clip appliers for insertion through smaller access ports, i.e., trocar cannulas, to minimize patient body openings. In particular, there is a need for a 5 mm clip applier that could fit through a 5 mm trocar. To fit through a 5 mm trocar diameter, several parameters have to be considered. First, to qualify as a medium clip, the unclosed configuration of the clip must be of sufficient open width to fit around desired tissue or other structure and have a desired closed configuration. Second, the applier needs to be able to be inserted through the cannula without dropping the clip from the instrument jaws or inadvertently crimping the jaws to close the clip. Additionally, since the width of the jaws exceeds the width of the clip, the jaws need to fit through the 5 mm dimension of the trocar. Satisfying these objectives while still providing a universal handle that could handle different size clips would be advantageous for the reasons noted above. Thus, it would be advantageous to have a clip applier that meets the necessary dimensions of insertion through a 5 mm trocar, i.e., of sufficiently wide width to receive and properly form the clips but of sufficiently narrow width to pass through the trocar diameter, while ensuring a clip is not formed or lost during insertion, in a handle stroke that can accommodate different clip sizes.

SUMMARY OF THE INVENTION

The present invention in one aspect provides a surgical clip applier comprising a handle at a proximal portion, an elongated portion extending distally of the handle, a jaw mechanism at a distal portion including a pair of jaws movable to a closed position to crimp a clip held therein, a clip feeder mechanism movable in proximal and distal directions, and a puller mechanism movable in proximal and distal directions. The puller mechanism is operatively connected to the handle such that actuation of the handle a) moves the puller mechanism a first distance in the proximal direction; and b) moves the clip feeder mechanism a second distance in the proximal direction, the second distance being greater than the first distance.

Preferably, the second distance is twice the first distance. The clip applier preferably includes a camming mechanism operatively connected to the puller mechanism to close the jaws to crimp the clip held therein. The clip applier can further comprise a stroke increasing mechanism for effecting moving of the clip feeder mechanism the second distance and can include a drive belt. In some embodiments, the drive belt is connected to the clip feeder mechanism at a first fixation and connected to the puller mechanism at a second fixation. In other embodiments, the clip feeder mechanism is positioned in a clip magazine, and the drive belt is connected to the clip magazine at a first fixation and connected to the puller mechanism at a second fixation. In some embodiments, the first fixation and second fixation are on opposite sides of the drive belt. In some embodiments, the stroke increasing mechanism further comprises a first carrier and a second carrier, the drive belt connected to the first and second carriers, and the second carrier can be operatively connected to the puller mechanism and the first carrier can be operatively connected to the first carrier via the drive belt.

In accordance with another aspect of the present invention, a laparoscopic surgical clip applier is provided comprising a handle at a proximal portion, an elongated portion extending distally of the handle, a jaw mechanism at a distal portion including a pair of jaws movable to a closed position to crimp a clip held therein and insertable through a trocar cannula without a clip positioned in the jaws, a puller mechanism operatively connected to the handle, and a clip feeder mechanism movable in proximal and distal directions, wherein proximal movement of the puller mechanism effects distal movement of the clip feeder mechanism to feed a clip into the jaws.

The clip applier preferably includes a stroke increasing mechanism, wherein movement of the handle moves the puller mechanism a first distance in a proximal direction to close the jaws and moves the clip feeder mechanism a second distance in a distal direction, the second distance being greater than the first distance. The second distance is preferably twice the first distance. The puller mechanism effects proximal movement of a cam mechanism to close the jaws of the jaw mechanism. In some embodiments, the stroke increasing mechanism includes a first traveler, a second traveler and a drive belt, wherein movement of the first traveler in a first direction effects movement of the drive belt to move the second traveler in a second direction opposite the first direction. In some embodiments, the drive belt has first loop connected to the first traveler and a second loop movable along a track in a housing of the stroke increasing mechanism, and the second traveler can be connected to the clip feeder mechanism and the first traveler can be connected to the puller mechanism.

In accordance with another aspect of the present invention, a laparoscopic surgical clip applier dimensioned for insertion through a five millimeter trocar cannula is provided comprising a handle at a proximal portion, an elongated portion extending distally of the handle, and a jaw mechanism at a distal portion including a pair of jaws insertable through the trocar cannula without a clip positioned in the jaws and movable from an open position to a compressed position by the trocar cannula during insertion through the trocar cannula. The applier further includes a puller mechanism operatively connected to the handle, a camming mechanism operatively connected to the puller mechanism and movable with respect to the jaws to crimp a clip held therein and a stroke increasing mechanism, wherein due to the stroke increasing mechanism, movement of the handle moves the puller mechanism a first distance and moves a clip feeder a second distance in a reverse direction, the second distance being greater than first distance, and further retracts the camming mechanism to close the jaws. Preferably, the second distance is twice the first distance.

In some embodiments, the stroke increasing mechanism includes a first traveler, a second traveler and a drive belt, wherein movement of the first traveler in a first direction effects movement of the drive belt to move the second traveler in a second direction opposite the first direction. In some embodiments, the drive belt has first loop connected to the first traveler and a second loop movable along a track in a housing of the stroke increasing mechanism.

BRIEF DESCRIPTION OF THE DRAWINGS

Preferred embodiment(s) of the present disclosure are described herein with reference to the drawings wherein:

FIG. 5a is a side elevation of a rotary translator of the surgical clip applier of FIG. 1.

FIG. 5b is section view taken along line 5b-5b of FIG. 5a.

FIG. 5c is a front elevation of rotary translator of the surgical clip applier of FIG. 1.

FIG. 6a is a side elevation view of the rotary drum of the clip applier of FIG. 1.

FIG. 6b is a longitudinal section view of the rotary drum of FIG. 6a.

FIG. 6c is an elevational view of the front face of the rotary drum of FIG. 6a.

FIG. 6d is an elevational view of the rear face of the rotary drum of FIG. 6a.

FIG. 7 is a front elevation of the anti-backup disc of the clip applier of FIG. 1.

FIG. 8a is a side elevation view of the thumb wheel hub of the clip applier of FIG. 1.

FIG. 8b is a longitudinal section view of the thumb wheel hub of FIG. 8a.

FIG. 8c is an elevational view of the front face of the thumb wheel hub of FIG. 8a.

FIG. 8d is an elevational view of the rear face of the thumb wheel hub of FIG. 8a.

FIGS. 9a-g are sequential views of the anti-backup mechanism of FIG. 7 with the disc in (a) rear groove, (b) & (c) between grooves, (d) in front groove, (e) & (f) between grooves, and (g) again in rear groove, and with arrows indicating directions of permitted and prevented movement of operating handle and cartridge mechanism.

FIG. 11 is an exploded perspective view of the individual cartridge mechanism components of the clip applier of FIG. 1.

FIGS. 12a-b are sequential fragmentary perspective views of the puller bar/cam puller "lost motion" with related cartridge components.

FIGS. 14a, b, c, d and e are fragmentary section views of the sequence of (a) a clip loaded in the jaws ready to fire and clip fired, (b) next-in-line clip being detained, (c) line of clips in cartridge being indexed rearward, (d) next-in-line clip moved downward into loading position, and (e) next-in-line clip loaded into the jaws ready for firing.

FIG. 15B is an exploded perspective view of one embodiment of a clip applier having an alternate embodiment of the cartridge assembly (mechanism) and having the stroke doubling assembly of FIG. 15A.

FIG. 16A is a perspective view of the stroke doubling assembly of FIG. 15A.

FIG. 16B is a perspective view of the stroke doubling assembly of FIG. 15A with one of the body halves removed to show internal components.

FIG. 18 is a perspective view with components removed showing the stroke doubling assembly of FIG. 15A mounted within the cartridge assembly.

FIG. 19A is a bottom perspective view of the cartridge assembly of FIG. 15B.

FIG. 20A is an exploded side view in partial cross-section showing the stroke doubling assembly of FIG. 15A prior to assembly to the cartridge components.

FIGS. 20B and 20C show in side partial cross-sectional views the sequence of operation of the doubling mechanism of FIG. 15A, FIG. 21 is an exploded perspective view of an alternate embodiment of a clip applier of the present invention having an alternate embodiment of the stroke doubling mechanism.

FIG. 22A is an exploded perspective view of the cartridge assembly mechanism) of FIG. 21.

FIG. 22B is an exploded view of components of the cartridge assembly of FIG. 21, FIG. 22C is an exploded view of the clip magazine of the cartridge assembly of FIG. 21.

FIG. 22D is a bottom perspective view of the clip magazine of the cartridge assembly of FIG. 21.

FIG. 27A is a perspective view of the handle mechanism of the clip applier of FIG. 21 with a housing half removed to show internal components, the handle shown in the open position.

FIG. 27B is a perspective view of the handle mechanism of the clip applier of FIG. 21 with a housing half removed to show internal components, the handle shown in the closed position.

FIGS. 30A, 30B and 30C show the sequence of operation of the doubling/reversing mechanism of FIG. 28.

FIG. 31A is a perspective view of an embodiment of an elongated portion having an external and an internal seal of the present invention.

FIGS. 31B and 31C are exploded perspective views of the elongated portion of FIG. 31A.

FIG. 32 is an exploded view of an alternate embodiment having an internal seal of the present invention.

DETAILED DESCRIPTION OF THE PREFERRED EMBODIMENTS

Figure 1:
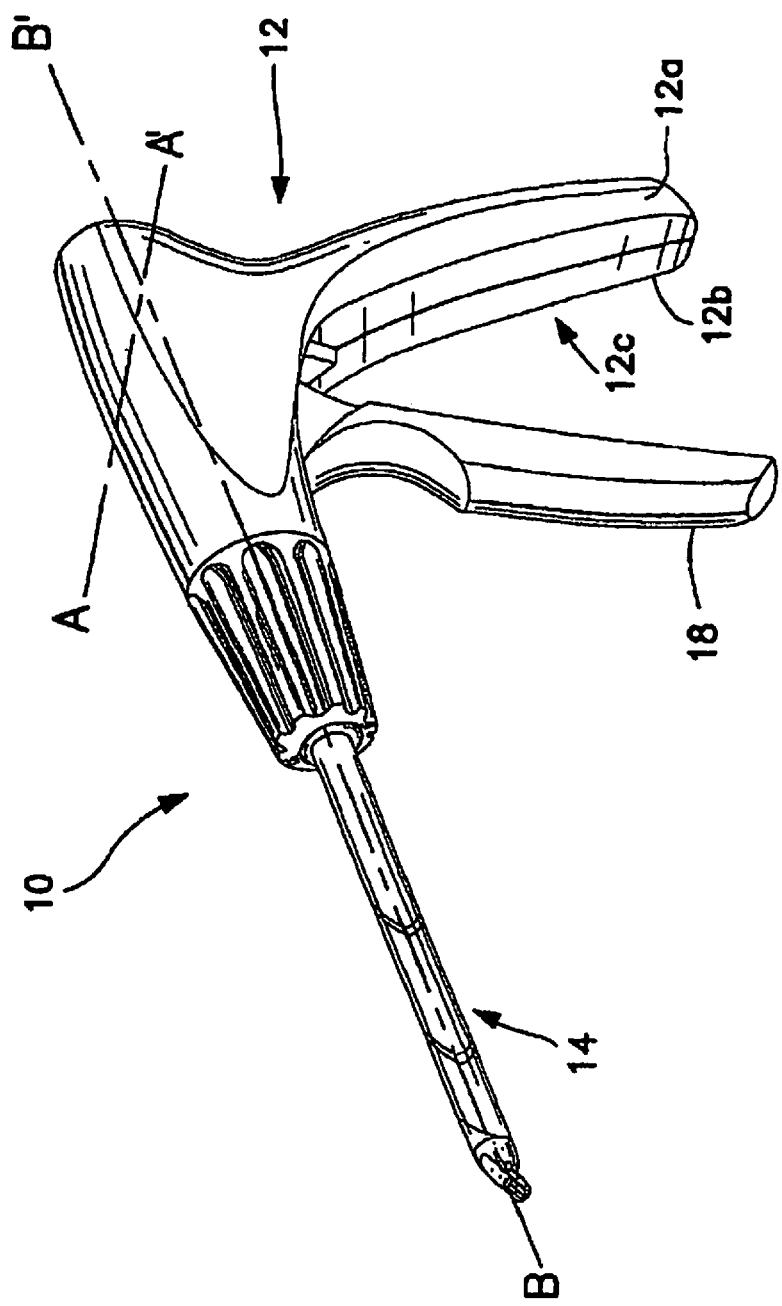
FIG. 1 is a perspective view of a surgical clip applicator (applicator) of the prior art with location of A-A' and B-B' axes.

Referring to the drawings, a repeating multi-clip applier of the prior art corresponding to the clip applier of U.S. Pat. No. 6,869,435 is first illustrated and discussed. The present application is an improvement to this clip applier of the prior art by a) increasing a stroke to provide a consistent stroke to accommodate different size clips and/or b) increasing a stroke and providing a reversing mechanism to enable use with smaller trocar cannulas in laparoscopic surgery. The features of the improved clip applier and their attendant advantages follows the discussion of the prior art clip applier. These features of the present invention can be used with the clip applier of the prior art described below or with other clip appliers, such as those described herein Prior Art Clip Applier The clip applier of the prior art is shown in FIGS. 1-14e and is designated generally by reference numeral 10 and includes an operating handle housing 12 and a clip applicator cartridge 14 extending from the housing 12.

Figure 2:
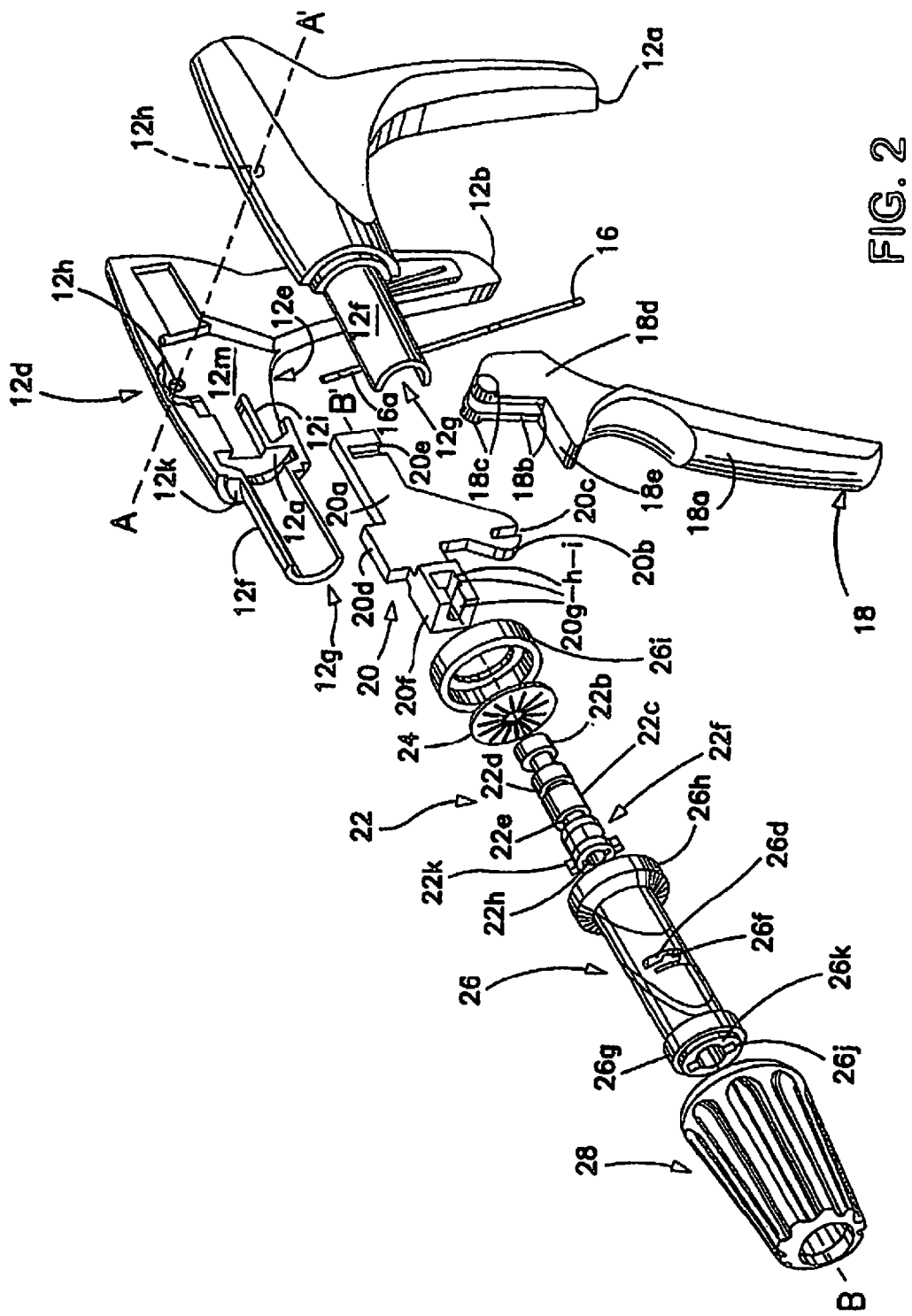
FIG. 2 is an exploded perspective view of the handle components of the surgical clip applicator of FIG. 1 including handle subassembly locating trigger pivot A-A' axis, and subassembly of fixed translator, rotary translator, anti-backup mechanism, rotatable drum, and thumb wheel aligned on B-B' axis.

The operating handle housing 12 shown in FIGS. 1-4 comprises left 12a and right 12b handle members defining a depending grip 12c, a center section 12d defining a central chamber 12e, and a forward cylindrical portion 12f defining a forward chamber 12g. Preferably, the interior defining surfaces 12e, 12g of the right handle member shown in FIG. 2 are substantially the same as the corresponding interior surfaces of the left handle member. The handle members are joined along a mid-plane and together receive handle operating components within the central and forward chambers. The handle members define a depending pistol type grip which receives a bar spring 16 forming part of the applier mechanism.

A trigger 18 for actuating applier mechanisms is mounted on the housing for pivotal movement about axis A-A'. The trigger includes a depending grip portion 18a integral with upwardly extending arms 18b fitted with pivot pins 18c received in corresponding hubs 12h located within housing central chamber and defining the A-A' axis. The outer surfaces 18d of the trigger arms are in surface contact with the adjacent inner surfaces 12m of the housing central chamber so as to confine trigger movement to a smooth circular movement about axis A-A'.

The trigger has a forwardly projecting shoulder 18e for engaging a plate 12i affixed to the housing at the central chamber for the purpose of establishing the forward limit of travel of the trigger about axis A-A' under the force of the bar spring 16 acting through fixed translator 20.

The trigger when pulled transmits motion to the clip cartridge mechanism 14a (FIG. 11) through the intermediation of fixed translator slide 20 and a rotary translator 22. The trigger cooperates with the fixed translator slide 20 to provide reciprocal rectilinear motion of predetermined excursion along B-B' axis, and the fixed translator slide cooperates with the rotary translator 22 to transmit reciprocal rectilinear motion of predetermined excursion and to accommodate 360 degree rotation about the B-B' axis of the rotary translator. In this way, the actuating mechanism 14a of the clip cartridge receives reciprocating rectilinear motion of fixed excursion while the clip cartridge is free to rotate 360 degrees in either direction about the applicator B-B' axis.

The fixed translator 20 functions as a slide which determines its contour. The fixed translator has an elongate body 20a with depending leg 20b having an open slot 20c defining a drive pin recess, an upper block 20d, a spring recess 20e, and an open front cage 20f. The fixed translator and the trigger form a subassembly with the translator located between the arms 18b of the trigger, and with the drive pin recess 20c fitted over a drive pin 18f (FIGS. 3, 4) positioned between the trigger arms. The location of the fixed translator between the upwardly extending arms of the trigger helps prevent the trigger arm pivot pins from popping out of their A-A' axis hubs 12h. When assembled with the operating handle housing, the fixed translator slides along central chamber surfaces 12m on either side of the trigger subassembly. The central chamber also accommodates the upper block 20d which in cooperation with the chamber walls limits forward and rearward movement of the trigger/fixed translator subassembly. The upper tip 16a of the bar spring fits into the spring recess 20e to provide a forward bias to the subassembly. So a pull of the trigger against the spring produces a circular trigger motion, i.e., a pivoting motion about axis A-A', which is received by the fixed translator as a rectilinear movement of excursion fixed by the interior contours of the central chamber and the upper block of the fixed translator. The drive pin recess 20c accommodates curvilinear movement of the trigger drive pin 18f and rectilinear movement of the translator. The front cage 20f of the fixed translator has an open front 20g, interior lip 20h, and open side 20i to receive and retain rotary translator 22.

The rotary translator 22 (FIGS. 2, 3 and 5) forms a subassembly with an anti-backup mechanism 24, a rotatable drum 26, and a thumb wheel hub 28 which subassembly interconnects the fixed translator 20 and the clip cartridge 14 for performing the functions of transmitting reciprocating rectilinear motion with a fixed excursion, accommodating rotary motion of the clip cartridge, enabling mounting and disconnecting of the clip cartridge from the operating handle, and providing an anti-backup capability for the operating handle and cartridge mechanism.

The rotary translator 22 (FIGS. 2, 5) comprises an elongate generally cylindrical shaft 22a with a rear flange 22b for connection to the fixed translator cage 20f so as to accommodate rectilinear motion of the rotary translator and fixed translator as a unit, and to accommodate rotary motion of the translator about the B-B' axis independent of the fixed translator. The center section 22c of the rotary translator shaft has spaced anti-backup grooves 22d, 22e with the distance between the grooves being approximately equal to the distance of reciprocating rectilinear motion of the fixed translator and, as becomes clear below, equal to the rectilinear excursion of the clip applicator mechanism. The intermediate cylindrical surface 22c of the rotary translator cooperates with an anti-backup disc 24 described more particularly next below. The rotary translator further includes a front end cage 22f for connection to the clip cartridge mechanism 14a. The front end cage is defined by a front flange 22g with a key hole 22h through its front face, a set of four interior, longitudinally extending shoulders 22i, and a pair of knobs 22k projecting radially from the flange rim. The rotary translator fits within a rotatable drum 26 (FIGS. 2, 6) which drum integrates subassembly components.

The rotary drum 26 is in the general form of a cylindrical sleeve 26a for orientation along the B-B' axis, with diametrically opposed interior grooves 26b extending the full length of the interior surface 26c of the sleeve, a pair of radially opposed slots 26d, 26e extending through the sleeve wall 26a, an integral wall spring 26f (FIG. 2) adjacent one of the slots 26d, a front end flange 26g, and an enlarged rear end flange 26h. The front flange includes a key hole 26j in front face 26k.

Figure 3:
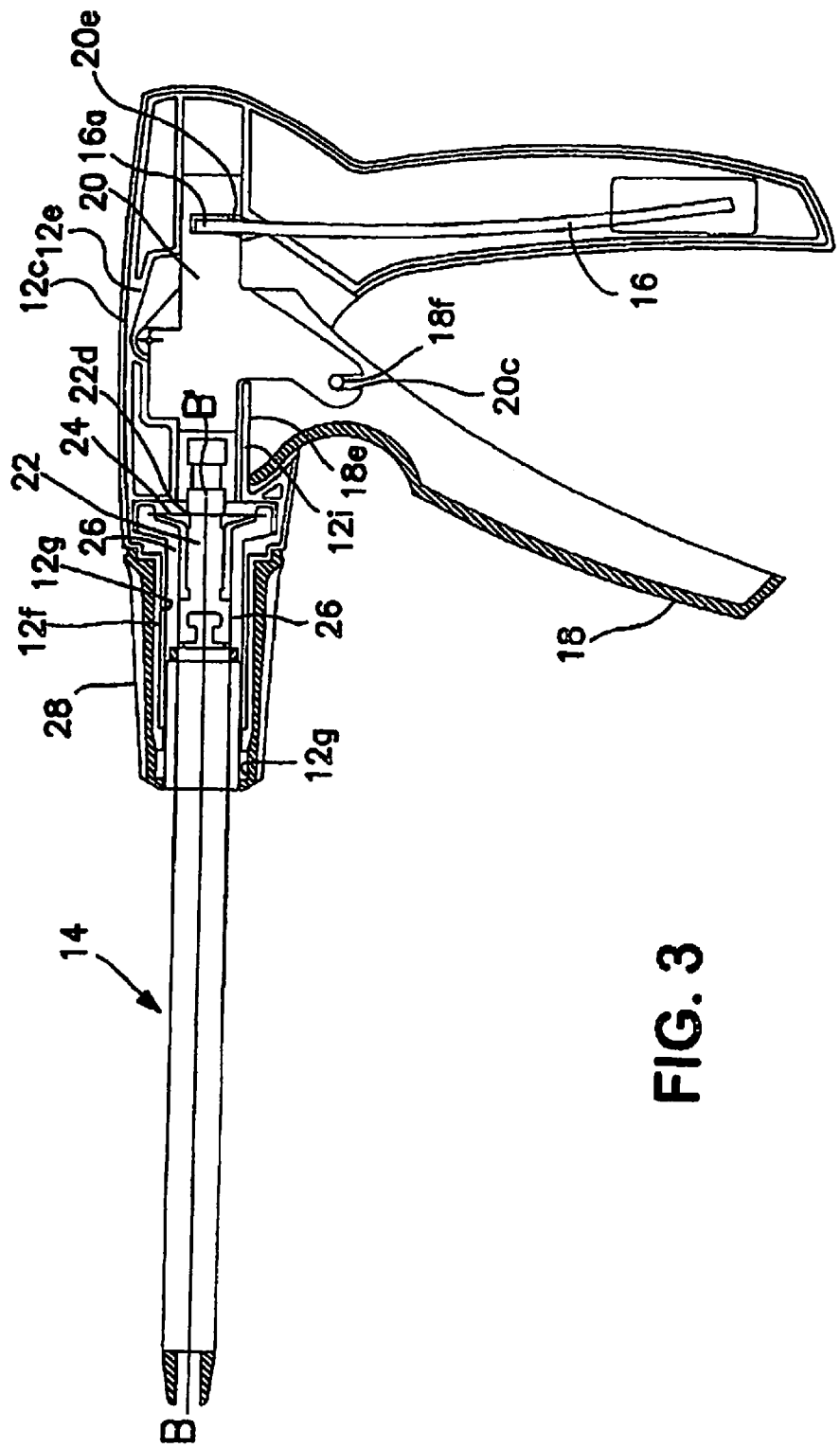
FIG. 3 is a side elevation view of the applicator of FIG. 1 with the operating handle housing partially in section and with the handle in the release position.
Figure 4:
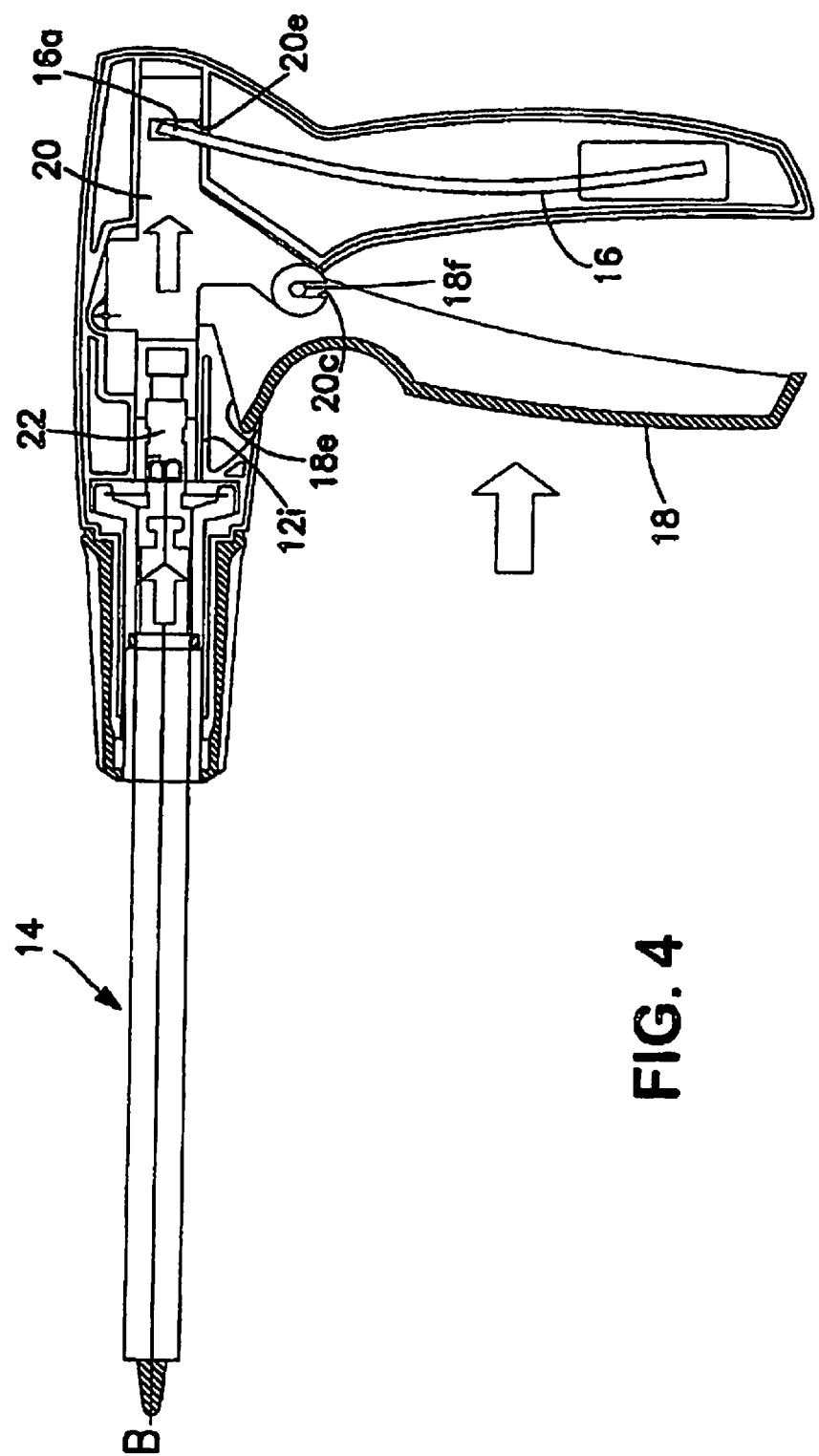
FIG. 4 is a side elevation view of the applicator of FIG. 1 with the operating handle housing partially in section and with the handle in the pull (actuated) position.

The rotary drum subassembly 22, 24, 26 comprises the rotary translator 22 positioned axially within the drum 26 with knobs 22k in interior grooves 26b. An anti-backup disc 24 (FIGS. 2, 3 and 7), defined by an open center 24a and slots extending radially from the center to define a plurality of inwardly directed spring fingers 24c, fits onto the rotary translator 22 and is assembled to the enlarged rear end flange 26h of the rotary drum by means of a drum cap 26i. In normal position of the clip applicator with the trigger released, the anti-backup spring fingers 24c are located in the rear anti-backup groove as shown in FIG. 3.

This rotary drum subassembly is then assembled into the forward chamber 12g of the operating handle housing with drum cap 26i fitted into chamber recess 12n (FIG. 2), with the drum front end flange 26g abutting a front rim of the front chamber, and with the rear flange 22b of the rotatable translator positioned within the cage 20f of the fixed translator.

A thumb wheel hub 28 (FIGS. 2, 3, and 8) with cylindrical interior surface 28a, tapered fluted exterior 28b, and front end retaining lip 28c fits over the handle front chamber 12f in abutment with housing exterior shoulder 12k and in abutment with the rotary drum front flange 26g.

The rotary drum subassembly within the operating handle housing is now ready to receive the removable clip cartridge and to impart both reciprocating rectilinear movement to the cartridge and to accommodate rotary movement of the cartridge.

The operation of the anti-backup mechanism is illustrated in FIGS. 9a-g.

As pointed out above, the center section 22c of the rotary translator shaft has spaced anti-backup grooves 22d, 22e with the distance between the grooves being approximately equal to the distance of reciprocating rectilinear motion of the fixed translator and equal to the rectilinear excursion of the clip applicator mechanism.

In the mechanism position of FIGS. 3 and 9a, the handle trigger 18 is in released position with the anti-backup disc 24 in registry with the rear anti-backup groove 22d of the rotary translator 22. When the trigger is pulled (FIG. 4) (for crimping and applying a clip at a surgical site), the rotary translator moves in the direction of arrow 9a. As the rotary translator continues movement, the spring fingers 24c of the disc engage the outer surface 22c of the rotary translator in the manner shown in FIGS. 9b-c. The anti-backup mechanism applied by the canted spring fingers 24c (FIGS. 9b-c) to the outer surface 22c of the rotary translator permits continued movement in the direction of arrow 9*a* and prevents movement in the opposite direction of arrow 9*b*. If a surgeon releases the trigger with less than a full pull stroke leaving anti-backup components in the position of FIG. 9*c*, for example, the anti-backup mechanism holds the rotary translator in position against the bias of bar spring 16 which tends to return the trigger to release position. In this FIG. 9*c* hold position, the applicator jaws retain the partially crimped clip preventing it from falling into a surgical site. A continuing pull of the trigger (in direction of arrow 9*a*) moves the rotary translator through the position of FIG. 9*c* to the position of FIG. 9*d* in which the spring fingers 24*c* enter the forward groove 22*e*.

In this position (FIG. 9*d*), the rotary translator may now be moved forward (by releasing the trigger and by force of return spring 16) in the direction of arrow 9*c*. In this forward movement, the spring fingers 24*c* are effective to allow continued forward movement while preventing movement in the direction of arrow 9*e*. If the handle trigger is held by a surgeon with components as in FIG. 9*f*, the anti-backup mechanism will prevent the surgeon from pulling the trigger in the direction of arrow 9*e*. The surgeon must allow full release of the trigger to component position of FIG. 9*g*. Direction of movement can be changed again when the spring fingers 24*c* enter the rear groove 22*e* as in FIG. 9*g*.

The clip cartridge 14 (FIGS. 10*a-c*) includes a tube 14*b* with its handle end having radially projecting positioning pins 14*c* emerging from end slots 14*d* (FIG. 11) in the tube, and an end 14*e* (FIG. 12) slot for passing the end of a puller bar 30 while maintaining radial alignment of the pins and puller bar. The puller bar terminates in a T shape flange 30*a*.

Referring to FIGS. 2, 5, 6 and 10*a-c*, for assembly of clip cartridge 14 and operating handle 12: (a) the clip cartridge 14 is inserted through keyhole 26*j* into the front end of the rotary drum 26 with cartridge positioning pins 14*c* entering interior drum slots 26*b*; (b) the T flange 30*a* projecting through cartridge end slot is in fixed radial orientation in relation to the positioning pins 14*c*; (c) the T flange approaches end face 22*m* of the rotary translator with the T flange in axial registry with the keyhole 22*h* in the front face of cage flange 22*f* (FIG. 2); (d) the T flange passes through the keyhole 22*h* into the rotary translator cage 22*f*; and (e) the cartridge is rotated (arrow 10*a*) on B-B' axis with cartridge pins 14*c* entering radial drum slots 26*d*, 26*e* (FIG. 6) and the T flange coming to rest against the rotary translator interior cage shoulders 22*i* (FIG. 5).

The slot spring 26*f* (FIG. 2) engages one of the pins 14*c* to hold the clip cartridge in assembled position with the handle.

The cartridge and operating handle are taken apart by reversing the assembly sequence.

Figure 10A:
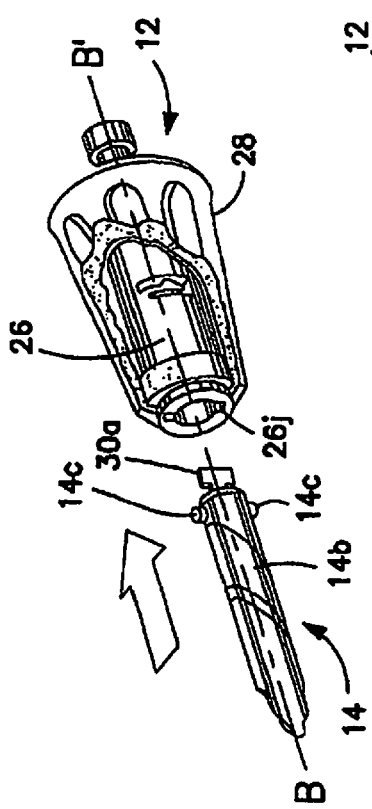
FIGS. 10a, b, and c are fragmentary perspective views of the sequence for inserting a clip applying cartridge magazine into a handle assembly housing of the clip applier of FIG. 1.
Figure 10B:
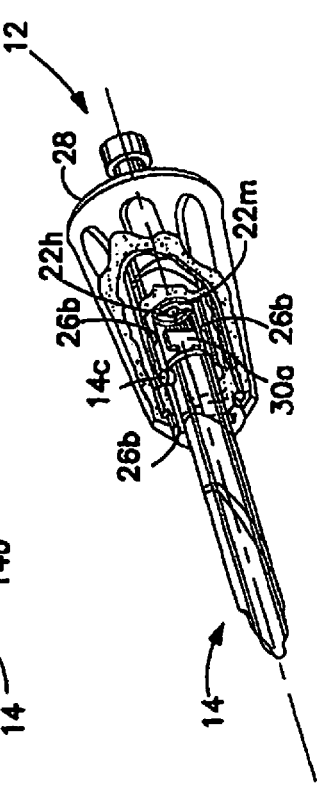
Figure 10C:
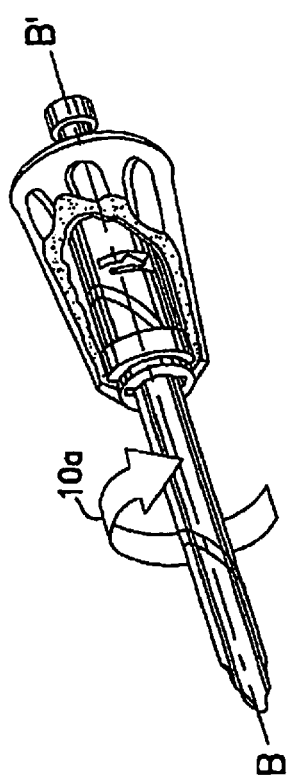
Figure 13:
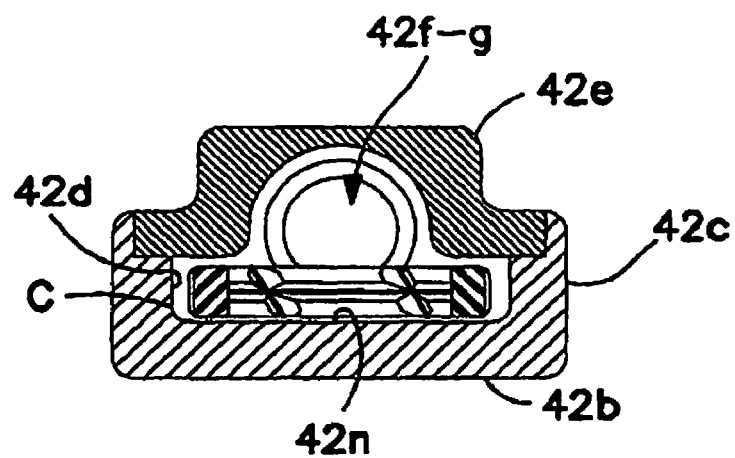
FIG. 13 is an enlarged section view taken along line 13-13 of FIG. 11.

In this clip applier assembly FIGS. 10*a-c*, the operating handle housing 12 may be considered stationary. The rotary drum subassembly (rotary translator 22, anti-backup mechanism 24 and rotary drum) together with thumb wheel hub 28 and the clip cartridge 14 are rotatable about the B-B' axis by manual application of torque to the thumb wheel and with the rear flange 22*b* of the rotary translator rotating freely in fixed translator cage 20*f*. In this way the cartridge is rotatable clockwise and counter clockwise as desired.

A pull on the trigger against the force of bar spring produces unitary rearward rectilinear movement of the fixed translator, the rotary translator passing through the stationary spring fingers of the anti-backup disc, and the puller bar emerging from within the cartridge casing until the trigger and fixed translator reach the end of travel and with the anti-backup disc spring fingers positioned at the front groove. The rearward excursion is now complete, and when the trigger is released, the bar spring urges the fixed translator forward until all components reach normal position.

In the event a pull on the trigger is released without reaching the full extent of rectilinear motion, the anti-back up spring fingers will not have reached their front groove remaining instead in contact with the outer surface of the rotary translator. The spring fingers in contact with outer surface function as a brake against the action of the bar spring tending to force the released components to return to normal position. In this partial pull condition of the trigger a clip has been crimped in the instrument jaws which clip will fall out of the jaws into a surgical site if the jaws reopen by return of the mechanism to normal position. So the anti-backup mechanism retains the instrument in "partial pull position" against the normalizing force of the bar spring and most importantly prevents fallout from the jaws of a partially crimped clip. The anti-backup device retaining action is removed simply by means of a full pull on the trigger causing the spring fingers to enter the forward groove where they can go "over center" thereafter permitting the rotary translator to pass through the spring fingers. It is to be noted that the anti-backup mechanism is effective in both directions. The anti-backup mechanism has effect when the trigger is released after a full pull so that if there is a "partial release" of the trigger, the trigger must nonetheless return to normal position with full release of the trigger before allowing the trigger to be pulled. The design requirement for full release achieved by the anti-backup mechanism prevents double loading of clips into cartridge jaws.

It is a further aspect of the anti-backup mechanism that the cartridge may be rotated on the B-B' axis as the anti-backup mechanism holds the instrument in partial pull position enabling a surgeon to adjust cartridge or jaw position even after a partial pull has occurred.

The clip cartridge 14 FIGS. 11-14*a-e* comprises an applicator housing tube 32, upper cartridge shell 34 and lower cartridge shell 36 connected to the operating handle housing as described above. The applicator housing upper 34 and lower 36 shells are elongate open ended channels having locating pins 14*c* serving to connect the cartridge to the handle as described above. The channels together define the end slot 14*e* (FIG. 12) through which the puller bar end 30*a* extends into the operating handle. The clip applicator housing encloses and forms part of a clip applicator mechanism 14*a*. In the following description, the applicator housing upper and lower shells 34, 36 are regarded as stationary in relation to movement of the applicator mechanism components.

The lower cartridge shell 36 has an anchor pin 36*a* affixed to the channel base interior 36*b*. The lower cartridge shell receives a cam puller bar 38 and coil spring 38*a* for sliding movement, and clip applicator jaws 40 mounted on the anchor pin 36*a*. The cartridge puller bar 30 overlies the cam puller bar 38.

The elongate cartridge puller bar 30 is located in the applicator lower shell 36*c* with the bar connected at its T shape rear end 30*a* to the rotary translator for receiving linear reciprocating motion with respect to the stationary lower shell 36 for each cycle of the handle operating trigger. The cartridge puller bar toward its front end includes laterally extending tabs 30*b* which cooperate with the cam puller bar 38. The cartridge puller bar also has a round hole 30*c* for receiving a magazine pin 42*a* depending from the underside of a clip magazine 42 by which the cartridge puller bar actuates the clip magazine. The magazine pin also passes through an elongate slot in a stationary clip plate 41.

The cam puller 38 occupies the lower shell beneath the cartridge puller bar and the clip applicator jaws. The cam puller bar is fitted with upstanding cooperating cam members 38b for closing and opening the clip applicator jaws 40. The cam puller bar includes a rear tang 38c and coil spring 38a accommodated in a recess 36b in the lower shell. The cam puller further includes an anchor pin slot 38d to accommodate reciprocal movement of the cam puller past the anchor pin 36a in the base channel and a cartridge pin slot 38e for accommodating movement of the cam puller past the cartridge pin 42a fitted to the underside of the clip supply magazine. The cam puller is fitted with spaced sets of upwardly extending tabs 38f and 38g for cooperating with the cartridge puller bar lateral tabs 30b.

The cam puller 38 is urged by coil spring 38a toward the forward end (i.e., the jaws end) of the clip cartridge so as to leave the clip applicator jaws 40 normally open. The cartridge puller bar 30 is normally forward under the influence of the handle bar spring with puller tabs 30b abutting the forward set of cam puller tabs 38f. When the trigger handle is pulled (FIG. 12a), the cartridge puller bar 30 moves rearward (with lost motion or dwell between cam puller bar forward 38f and rear 38g tab sets) until the cartridge puller tabs 30b engage the rear set 38g of cam puller tabs thereby drawing the cam puller 38 to the rear against its coil spring for closing the applicator jaws. The cartridge pin slot 38e accommodates cam puller movement past the cartridge channel pin 42a during the time of lost motion between the cartridge puller bar 30 and cam puller tab sets 38f-g.

Lost motion of the cam puller bar ensures that the applicator jaws remain open for a portion of the rearward movement of the cartridge puller bar before the jaws close and crimp a clip in surgery. It is desirable to crimp the clip at the end of rearward travel so as to provide the surgeon with a natural feel for releasing the handle. Lost motion also has significance on the forward stroke of the clip applicator mechanism by ensuring the applicator jaws are open to receive a clip during the forward stroke of the applicator mechanism, as is to be fully understood with description of the clip supply magazine and associated mechanisms below.

Clip applying jaws 40 comprising spring biased arms 40c-d are mounted at opening 40e to anchor pin 36a on the applicator lower shell with the jaws projecting from the front end of the base channel.

FIGS. 11 and 12a-b illustrate spring biased applicator jaws affixed to the applicator housing anchor pin 36a with spring biased arms 40c-d able to move from open-to-closed-to-open positions in applying a clip. The inner surfaces 40f of the jaws are recessed to form cooperating channels for movement of each clip into the jaws. The outer surfaces of the jaws have aligned recesses 40b and inclined cam surfaces 40g cooperating with aligned cam members 38b affixed to the cam puller for the purpose of closing the jaws for each rearward excursion of the cartridge puller bar 30. The jaws are released to spring open on the forward excursion of the cam puller placing the cam members within the recesses 40b. The normal position for the cam puller 38 and jaws 40 occurs with the cam puller at the forward end of linear excursion, with the jaws open and with the cam puller cam members 38b in an inactive position with respect to applicator jaws as in FIG. 12b.

The cartridge applicator mechanism includes a clip supply magazine 42 (FIGS. 11, 13 and 14a-e) which is affixed to and reciprocates with the cartridge puller bar 30 by means of magazine pin 42a at the underside the magazine fitting into hole in the puller bar. The clip supply magazine and cartridge puller bar are separated by a stationary clip plate 41 having a central slot 41a to accommodate sliding movement of the clip supply magazine 42 and its pin 42a by means of the cartridge puller bar. The clip plate 41 includes a cam slot 41b and front end clip ramp 41c cooperating with the clip supply channel as described below.

The clip supply magazine 42 (FIGS. 11, 13) includes an elongate base plate 42b with upstanding sides 42c to define a central channel 42d for receiving and retaining a line of clips C. A dome 42e extends between the sides for receiving an elongate clip follower 42f and coil spring 42g. The clip follower is positioned and retained in the clip supply magazine in engagement with the last clip C.sub.Z (FIG. 14) and is urged forward by the coil spring for advancing the line of clips along the supply channel. The clip follower has forwardly directed fingers 42h for engaging clip shoulders for constantly maintaining a force on the line of clips by means of the coil spring.

The clip supply magazine 42 (FIG. 11) has an integral forwardly extending pusher plate 42i preferably with notched front edge 42h conforming to clip contour for the purpose of pushing each clip into the jaws as it leaves the supply magazine.

A clip stop spring 42k (FIGS. 11, 14) with vertical tip 42m is formed integral in the base plate 42b of the clip magazine for gripping the leading clip C.sub.L at midpoint. The clip stop spring has a "spring set" wherein the spring is normally positioned or biased below the surface 42n of base plate (as in FIG. 14a) with the spring being accommodated in the cam slot 41b (FIGS. 11 and 14) of stationary clip plate 41 located underneath the magazine.

The clip plate 41 is fixed to the stationary housing by suitable means so that the back edge of the cam slot 41b urges the clip stop spring 42k and its tip upward into the path of clips C when the clip magazine moves rearward with the cartridge puller bar (FIGS. 14a-c). As noted above, the slot 41a in the clip plate accommodates reciprocal movement of the clip magazine/puller bar connecting pin 42a.

The housing upper shell 34 has depending from its inner surface a clip detent spring 44 (FIGS. 11, 14) and a guide ramp surface 34a for positioning clips for movement into clip applying jaws. The clip detent spring comprises a leaf spring 44a with spaced depending panels 44b-c of identical edge contour terminating in forwardly directed notches 44d for engaging the shoulders of a lead clip C.sub.L to separate the lead clip from the line as the line of clips and the clip magazine are pulled rearward by clip stop spring 44k and cartridge puller bar 30 with a pull of the operating trigger. On release of the trigger and consequent forward movement of the clip magazine (FIGS. 14d-e), the cartridge pusher plate 42i engages the rear surface of the detained lead clip C.sub.L and pushes it into the crimping jaws.

The action of clip moving components is shown in FIGS. 14a-e starting with FIG. 14a which shows components in forward position and a clip C.sub.J in the instrument jaws.

Referring to FIG. 14a, a first in line of clips C.sub.F is at rest under the detent spring notches 44d for the purpose of separating clip C.sub.F. The detent spring 44 is stationary in that it is affixed to the under side of the housing cover in position to capture and hold the lead clip C.sub.F at the end of the forward excursion of the cartridge puller bar and clip supply magazine. The detent spring takes and separates the lead clip C.sub.F from the clip line in preparation for movement of the lead clip into the applicator jaws on a subsequent applicator cycle. The detent spring separates clip C.sub.F by reaction as the inclined rear edges ride up (FIG. 14e) on forwardly moving clip C.sub.F and snap down (FIG. 14a) as the clip passes the shoulders. Such clip capture occurs as the puller bar and clip magazine reciprocate during operation of the applicator, as detailed below.

From the position of FIG. 14a, a rearward pull of the trigger begins immediate rearward sliding movement of clip supply magazine 42 with respect to stationary upper shell 42 and stationary clip plate 41. The clip detent spring 44 holds and separates clip $C_F$ from the line of clips. The line of clips moves rearward with the clip cartridge as clip stop spring 42k is cammed upward (FIG. 14b) by cam slot 41b in clip plate 41. As movement continues (FIG. 14c), the cartridge pusher plate 42i also moves rearward sliding underneath clip $C_F$ and coming to rest behind the clip (FIG. 14d) at the end of the rearward stroke of the operating handles. As pusher plate 42i slides behind clip $C_F$, the clip detent spring 44 (having a normal downward spring force) pushes clip $C_F$ downward into contact with clip ramp 41c. When the operating handles are released, beginning from the position of FIG. 14d and continuing to FIG. 14e, the clip cartridge pusher plate 42i engages clip $C_F$, pushes it forward between upper shell ramp surface 34a and clip plate ramp 41c and on into the instrument jaws. As this forward motion occurs, the clip detent spring 44 rides up on clip $C_L$ with notches 44d coming to rest behind the clip shoulder as illustrated in FIG. 14a.

The operation of clip applicator is as follows. The housing upper and lower shells are stationary with respect to movements of the component parts of the actuating mechanism. At the beginning of an operating cycle (or normal position), the handle trigger is in forward or release position, the cartridge puller bar and clip supply magazine are in forward position, the jaws are open holding a clip in position for surgical application, jaw actuating cam puller is in inactive position, the lead clip is in the capture position under clip detent spring, the cartridge pusher plate lies under the captured lead clip, the clip stop spring is inactive and lies in the clip plate cam slot below the surface of the pusher plate, the spring loaded clip follower engages the last in line clip, and the spring biased line of clips is in contact with lead clip $C_F$.

By squeezing the trigger, the puller bar and clip magazine move rearward relative to the stationary upper and lower shells and stationary clip plate to accomplish:

a. movement of the magazine pusher plate out of the jaws,
  b. continued movement of the pusher plate relative to the clip plate whereby the stop spring is cammed up so its tip grips the next in line clip $C_L$ and by continued rearward movement the stop spring separates the clip stack from the lead clip $C_F$;
  c. after an initial lost motion or dwell phase during which the jaws are open, engagement of cartridge puller bar tabs and cam puller tabs for pulling cams means along jaw cam surfaces to close the jaws and crimp a clip in surgical application,
  d. the captured clip $C_F$ is held in place under the clip detent spring;
  e. movement of the cartridge pusher plate from underneath captured clip $C_F$ into position behind clip $C_F$;
  f. downward movement of clip detent spring and clip $C_F$ on to the clip plate ramp and in front of the clip pusher plate; and by releasing the trigger, the cartridge puller bar and clip supply magazine move forward in relative movement to the stationary upper and lower shells and stationary clip plate to accomplish:
  g. disengagement of the cartridge puller bar tabs from the cam puller tabs and forward movement of the cam puller bar under the influence of its coil spring thereby moving cam means along the jaws cam surfaces into inactive position thereby opening the jaws;
  h. movement of the cartridge pusher plate to advance the captured clip $C_F$ into the jaws; and
  i. the cartridge pusher plate and stop spring move relative to the clip plate with the stop spring reentering its slot in the clip plate out of the path of the clip line so as to permit the next in line clip $C_L$ to advance along the surface of the pusher plate to deflect the clip detent spring and be captured as $C_F$.

The clip applicator of FIG. 2 can be made as a disposable cartridge to be inserted into a non-disposable handle with the cartridge removed from the handle and discarded after its clips are consumed. In a cartridge arrangement both the cartridge housing and rear end of the actuating rod have plug-in connections to the handle housing and link journal respectively.

The magazine pusher plate acts as a lock-out of the jaws after all the clips in the cartridge magazine have been used and there are none left. Such lock-out action occurs as the pusher plate without a clip to push itself enters the space between the crimping jaws and prevents the jaws from closing thereby indicating to the surgeon that there are no more clips to be applied.

Clip Appliers of the Present Invention

The present invention provides improvements to the aforedescribed clip applier of the prior art by providing a stroke increasing mechanism. The stroke increasing mechanisms/assemblies of the present invention can be utilized with the prior art clip applier of FIGS. 1-14, the other clip appliers disclosed herein or with other clip appliers.

There are two variations of the clip applier of the present invention which provide unique advantages. In one aspect, a mechanism is provided to increase a stroke, e.g., a doubling of the stroke, to provide a consistent handle stroke. This enables the same handle, i.e., a universal handle, to be used to apply different size clips, e.g., a medium clip (5.03 mm width/5.02 mm height) or a medium large clip (e.g., 4.50 mm width/8.00 mm height). In the absence of such mechanism, since a different stroke is necessary to apply a different sized clip, e.g., a clip of longer length, a different handle mechanism would be required for each size clip. Thus, this feature has manufacturing advantages, e.g., reduces overall manufacturing costs since a single type handle can be manufactured for applying different size clips. This also provides an advantage where a reusable handle and a disposable cartridge are desired. In the absence of such uniform handle, different handles would need to be manufactured and stocked by the user to accommodate different size clips, i.e., one handle for firing a series of clip of one size and another handle for firing a series of clips of another size. With the uniform consistent-stroke handle of the present invention, only one handle need be manufactured or stocked. This stroke doubling is achieved by the/belt system described in detail below. Various embodiments of this aspect are illustrated in FIGS. 15A-27B.

In another aspect of the present invention, providing an improvement over prior art clip appliers, a mechanism is provided which not only increases a stroke, e.g., a doubling of the stroke, to provide a consistent handle stroke but reverses the clip feeder movement so a clip is not fed into the jaws until after insertion of the clip applier through the trocar cannula. Thus, this universal handle can be used with clip appliers insertable through small trocars, e.g., a 5 mm trocar. This is achieved by providing a mechanism that keeps a clip out of the jaws during initial insertion of the clip applier through a trocar and loads the clip in the jaws after it is inserted through the trocar. Thus, the size of the clip, e.g., a medium or medium large clip, can be maintained even though the applier is inserted through a smaller trocar. Further, by loading the clip after insertion, the risk of crimping the clip during insertion or the clip becoming dislodged is eliminated, adding a safety advantage. Additionally, by providing a handle stroke which loads a clip and closes the jaws, the clip applier can be removed through the trocar before all clips are fired since in the normal position, a clip is not positioned in the jaws. Such design for use with a smaller trocar, without sacrificing clip performance, is achieved through the doubling/reversing belt system described in detail below. This aspect is shown in FIGS. 28-30C.

Turning first to FIGS. 15-20, a first embodiment of the stroke increasing mechanism (or stroke increasing assembly) is illustrated. Preferably, the mechanism (assembly) effects a doubling of the stroke so the mechanism of this embodiment is also referred to herein as the stroke doubling mechanism. However, it should also be appreciated that other increases in stroke are also contemplated and within the scope of the present invention to achieve the objectives of the present invention.

Figure 15A:
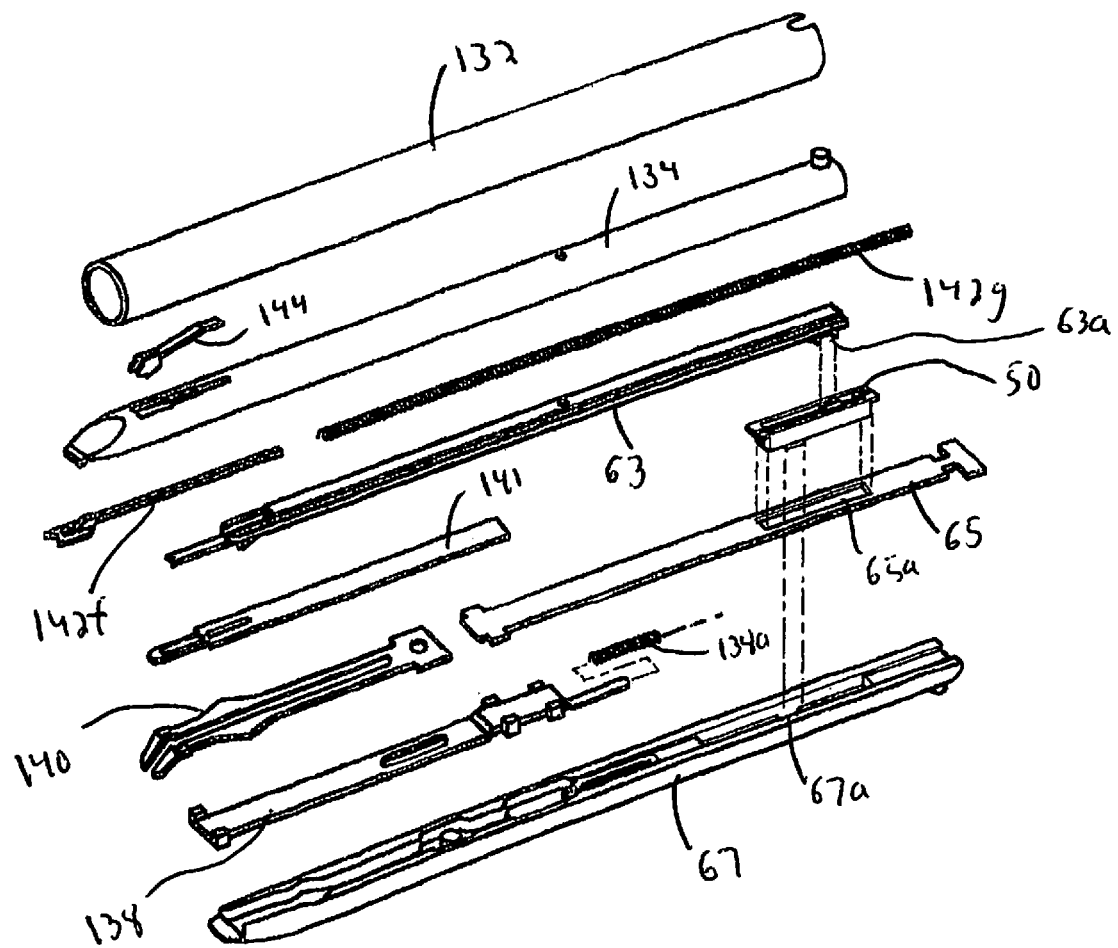
FIG. 15A is an exploded perspective view of the cartridge assembly (mechanism) components of a first embodiment of the present invention having a first embodiment of the stroke doubling assembly (mechanism).

The embodiment of FIG. 15A is identical to the embodiment of the prior art of FIGS. 1-14 except for the doubling mechanism and related components. Therefore, for brevity only the differences are discussed in detail. For convenience, like components to clip applier 10 of FIGS. 1-14 have been numbered in FIG. 15A in the "100 series" so that corresponding parts can readily be appreciated. For example, the cartridge components of FIG. 15A include an applicator housing tube 132 identical to tube 32 (forming an elongated portion), a clip detent spring 144 identical to spring 144, an upper shell 134 identical to shell 34, a clip follower 142f and coil spring 142g identical to clip follower 42f and coil spring 42g, respectively, a stationary clip plate 141 identical to clip plate 41, jaws 140 identical to jaws 40 and cam or camming mechanism 138 biased by coil spring 138a identical to cam 38 and spring 38a to close the jaws 140 upon proximal movement. These components are not discussed in more detail herein since their structure and function are identical to the structure and function of these components of FIGS. 1-14. Additionally, other features such as the handle, anti-backup mechanism, etc. are not shown since they are identical to that of FIGS. 1-14 and their description with respect to those Figures is fully applicable to the embodiment of FIG. 15A. FIG. 15A differs from the embodiment of FIG. 1-14 in the provision of the stroke doubling mechanism 50, also referred to herein as the stroke doubling assembly. Due to provision of the stroke doubling mechanism 50, the clip supply magazine 63, cam puller bar or puller mechanism 65 and lower cartridge shell 67 differ from these components of clip applier 10 of FIGS. 1-14 and therefore are not numbered in the "100 series" and are discussed in detail below in conjunction with doubling assembly 50. The stroke doubling mechanism 50 results in proximal movement of the cam puller 65 a distance X effecting a proximal movement of the clip feeder (or clip magazine) a distance 2X. As noted above, the second distance need not be 2X but can be other multiples of, or increases to, x.

Figure 15C:
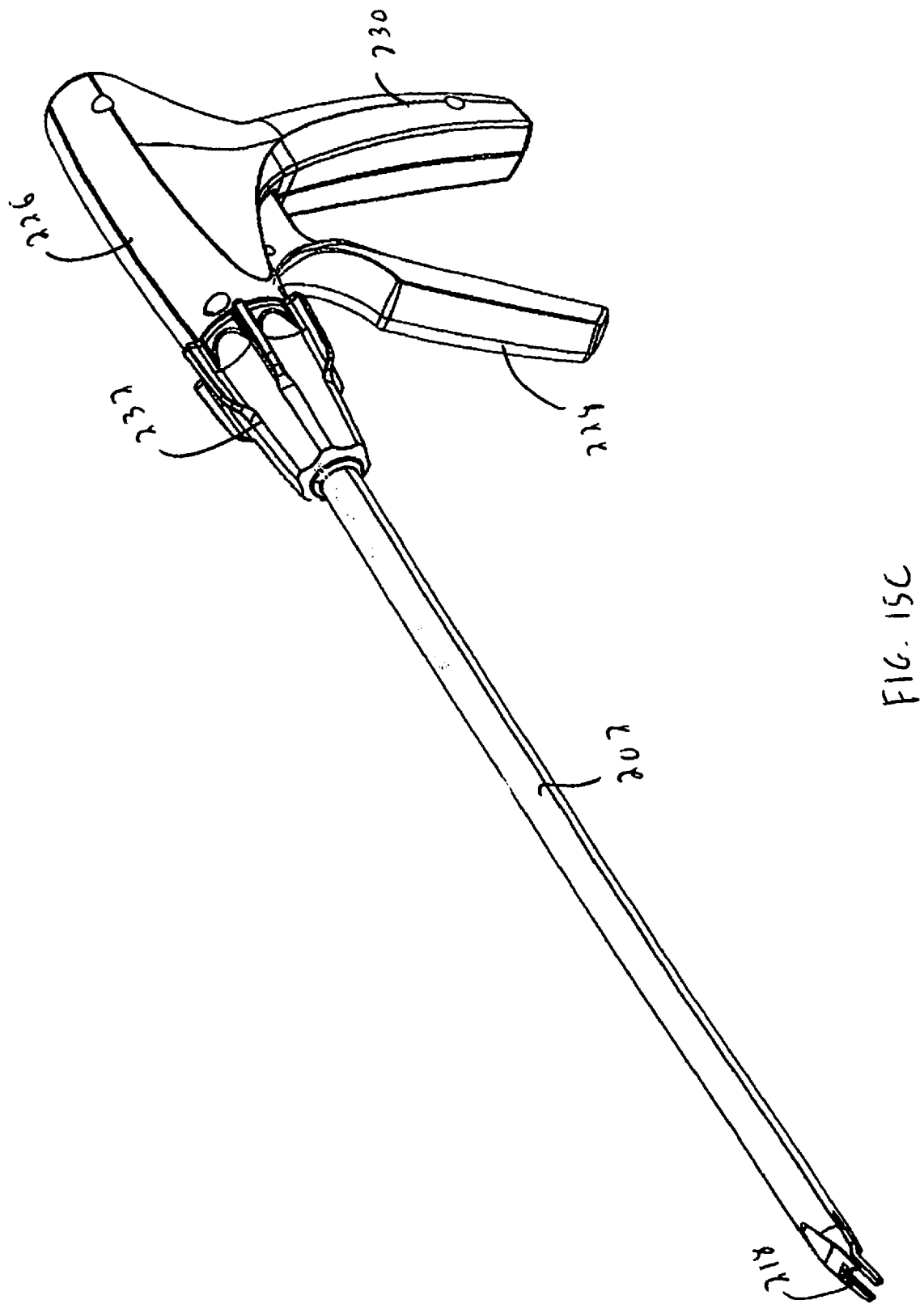
FIG. 15C is a perspective view of the clip applier of FIG. 15B shown in the open position.

The doubling mechanism 50 can also be used with other cartridge mechanisms such as that shown in FIGS. 15B and 15C. The cartridge mechanism of FIG. 15B operates in a similar fashion to the cartridge mechanism of FIG. 15A however some of the components are different. For example, the cartridge mechanism of FIG. 15B has a cover 202 and a chassis 224 which are assembled together forming an elongated portion of the instrument extending distally form the handle assembly 226. Positioned within the assembled cover 202 and chassis 224 are a clip pusher 206 biased by spring 208 for advancing the stack of clips 210, a clip detent 204 to engage and separate the lead clip, a clip track floor 212 to support the clips 214, a clip advancer or mechanism 216 to advance a lead clip 214 into jaws 217 of jaw mechanism 218, and a cam or camming mechanism 220 attached to a cam puller bar 222 or puller mechanism for proximal movement to cam the jaws 217 to a closed position. Note although the puller bar or puller mechanism 222 is shown as a bar, alternatively it could be shaped as a rod as in the embodiment of FIG. 21. Note the angle of the cam and jaws can be that disclosed in pending application Ser. No. 14/756,281, filed Aug. 20, 2015, the entire contents of which are incorporated herein by reference. The handle assembly 226 for actuating the cartridge components is shown in FIGS. 15B and 15C with the stationary handle or grip designated by reference numeral 230 and the movable handle to effect clip application and advancement designated by reference numeral 228. Squeezing of movable handle 238 effects retraction of puller bar 222 which effects retraction of clip feeder (advancer) 216 and retracts cam 220 to close the jaws 217. Release of the movable handle 238 to return to its original open position effects distal movement of puller bar 222 to its original position and distal movement of clip advancer 216 to its original position as described in detail below along with the discussion of the stroke increasing mechanism 50. Rotation knob 232 can be provided to rotate the elongated portion and/or cartridge to change the position of the jaws 217 of jaw mechanism 218. Other handle mechanisms, including those described below can also be utilized. The cartridge assembly can be permanently attached to the handle for a single use or alternatively it can be a separable and disposable cartridge, replaceable by another cartridge, for multiple uses in a single procedure. The stroke increasing mechanisms disclosed herein enables replacement of cartridges with different sized clips.

It should be appreciated that these cartridge mechanisms of FIGS. 15A and 15B are shown by way of example as other cartridge mechanisms, e.g., with variations of the illustrated components, can be configured to accommodate the unique stroke increasing mechanisms of FIG. 15A-20C.

Figure 17A:
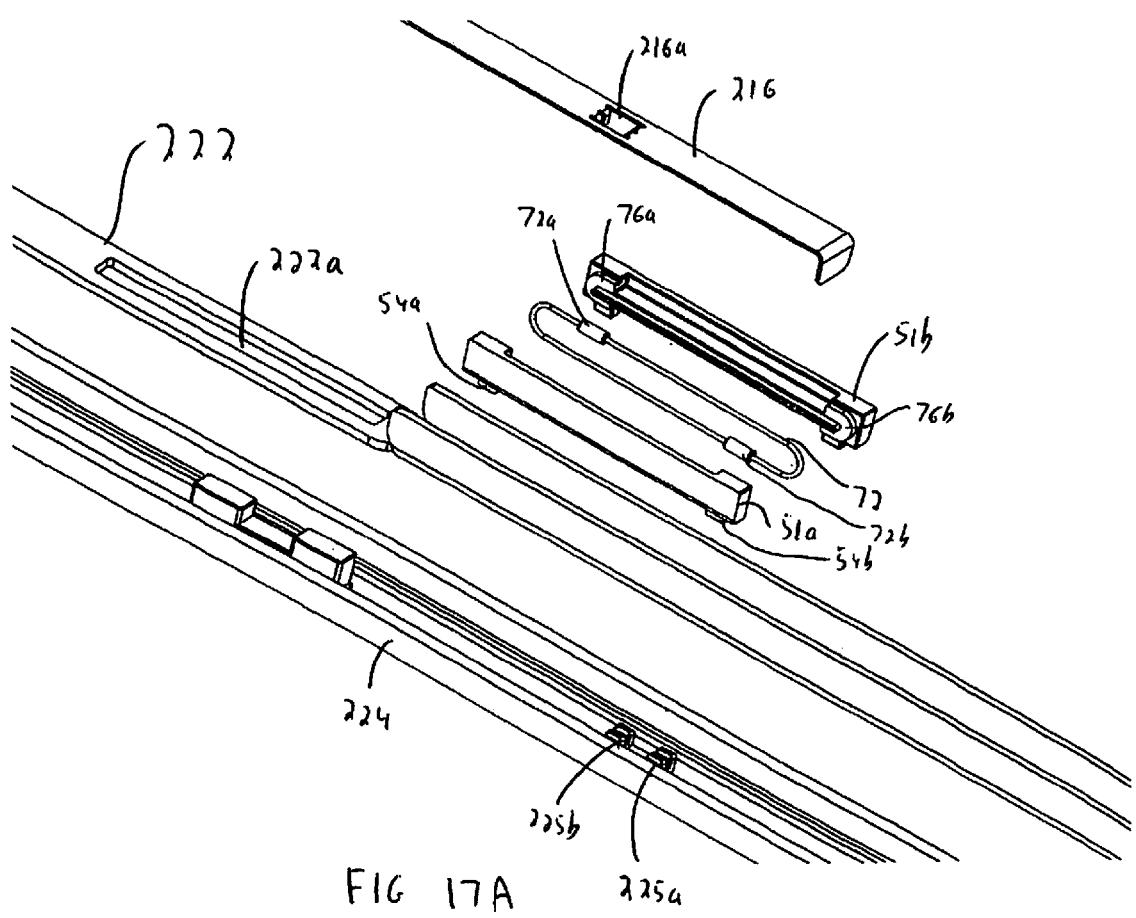
FIGS. 17A and 17B are exploded top views from different angles showing the stroke doubling assembly of FIG. 15A and components of the cartridge assembly of FIG. 15B.
Figure 17B:
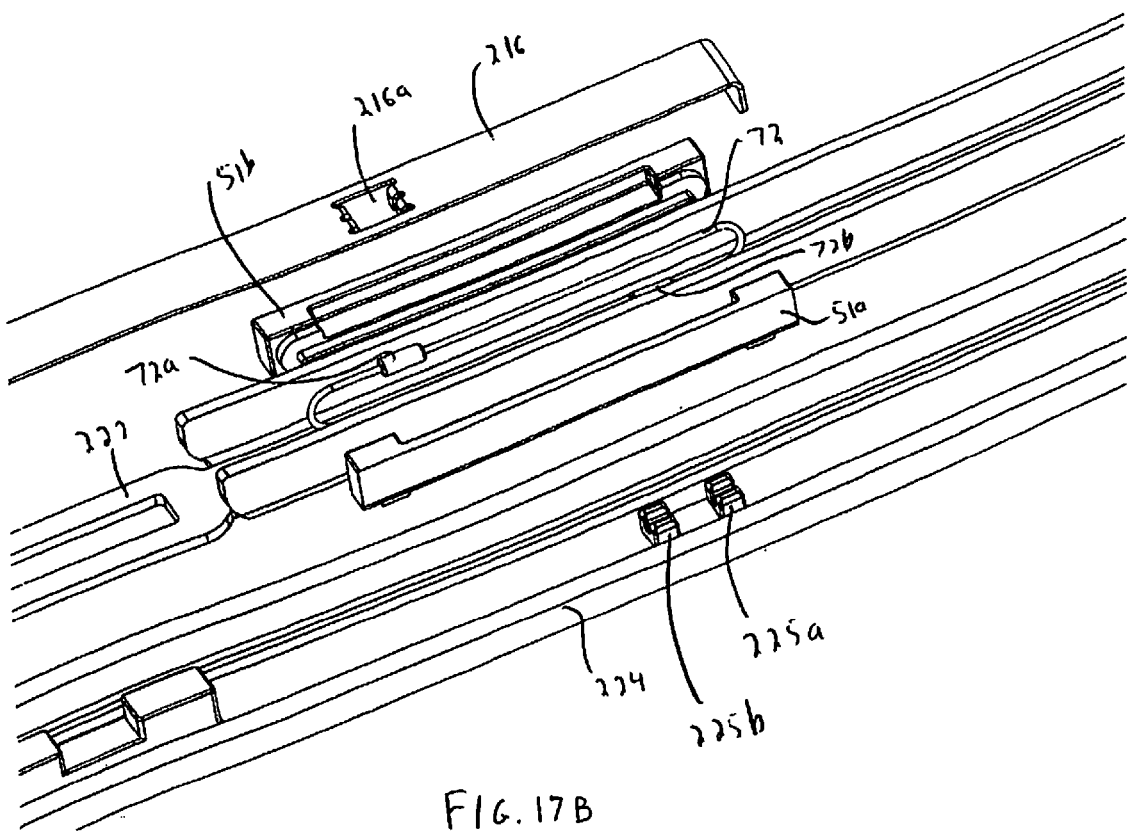
Figure 19B:
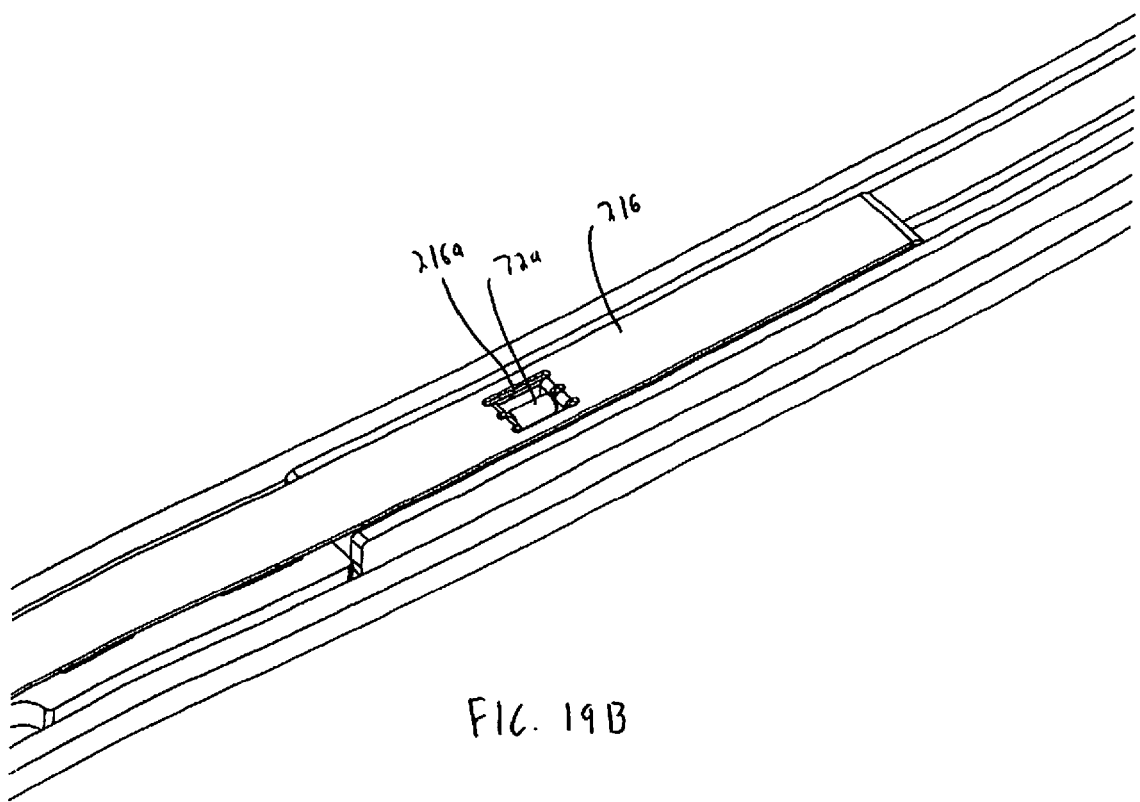
FIG. 19B is a top perspective view of the cartridge assembly of FIG. 15A.
Figure 77D:
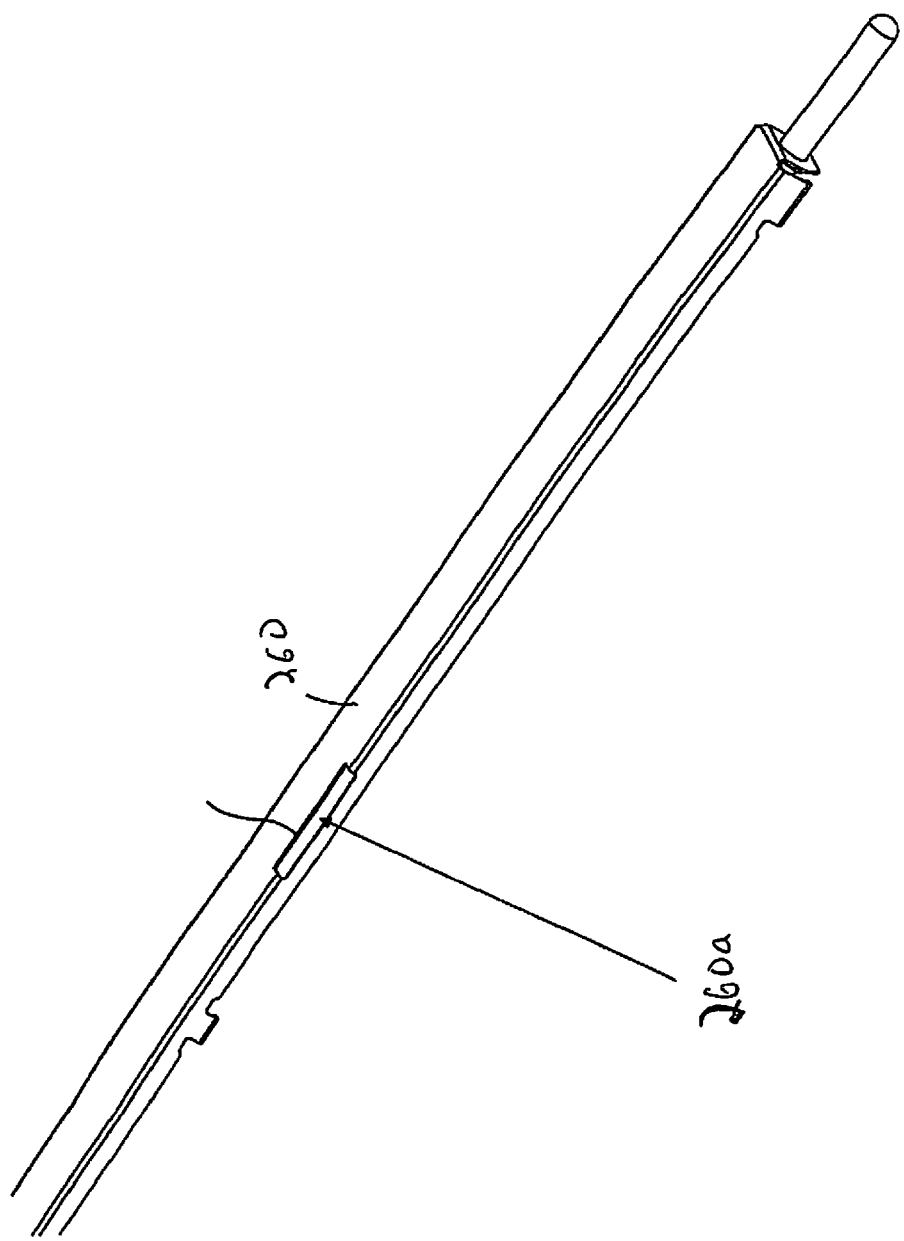
Figure 23:
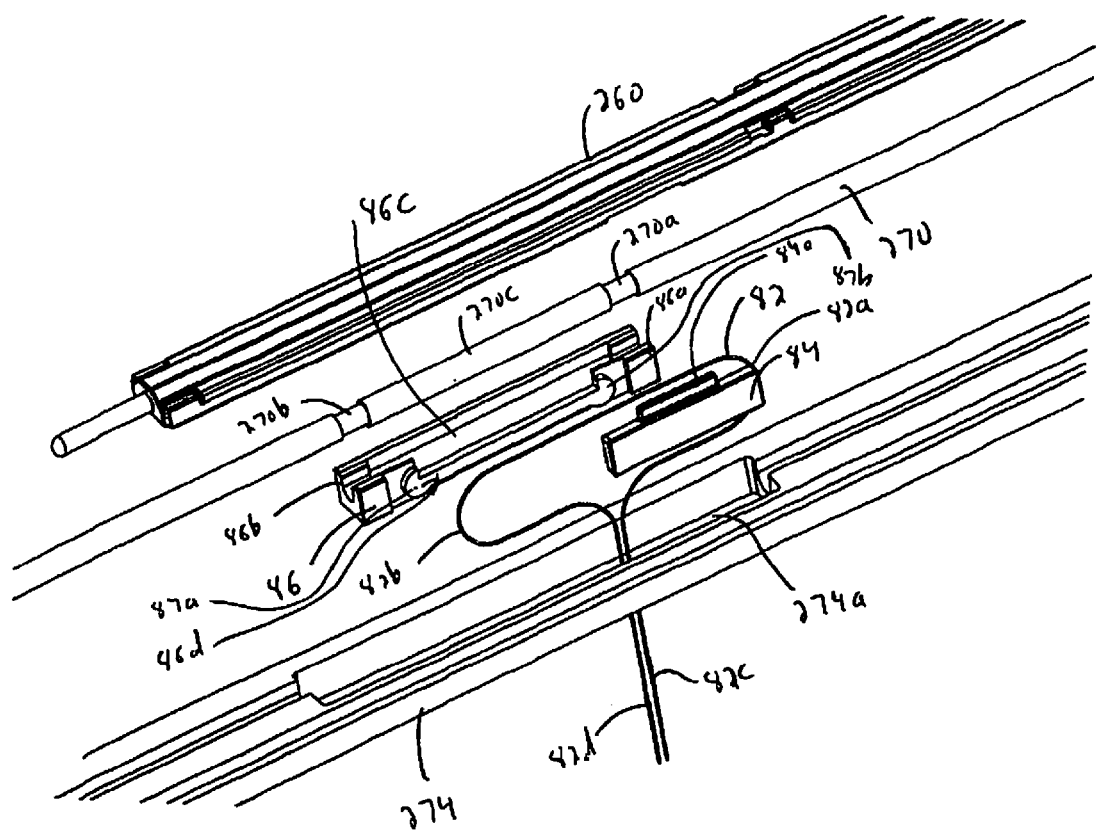
FIG. 23 is an exploded perspective view of certain components of the cartridge assembly and the stroke doubling mechanism of FIG. 21.

Turning now to the stroke increasing mechanism (also as noted above referred to herein in conjunction with the illustrated embodiment as the stroke doubling mechanism), and with reference to FIGS. 16A-19B, the doubling mechanism 50 has an outer body 51 having a proximal portion 52a, a distal portion 52b, a distal lower mounting tab 54b and a proximal lower mounting tab 54b. Outer body 51 can be composed of two body halves 51a, 51b as shown in FIG. 17. Note the terms "lower" and "upper" as used herein are with respect to the orientation shown in the drawings. Clearly, if the orientation changes, the reference to upper and lower would also change. The stroke doubling mechanism 50 results in proximal movement of the cam puller a distance X effecting a proximal movement of the clip feeder (or clip magazine) a distance 2X. As noted above, the second distance need not be 2X but can be other multiples of, or increases to, X.

Doubling mechanism 50 further includes a drive belt 72, arranged for movement in a longitudinal (axial) direction within the cartridge mechanism. The drive belt 72 is preferably a flexible high tensile low friction belt. Drive belt 72 has a top engagement member 72a, e.g. a ferrule 72a, and a bottom engagement member 72b, e.g., a ferrule 72b. The ferrules 72a, 72b are attached to the belt 72. Although shown as ferrules, other engagement or fixation mechanisms or members are also contemplated. The belt 72 has a proximal looped portion 73a and a distal looped portion 73b looped around respective proximal and distal round supports 76a, 76b (FIG. 17A) forming a track for travel of the belt 72. The body 51 has a proximal channel 74a and a distal channel 74b to provide space for the drive belt 72 and enable movement of the drive belt 72. A longitudinally extending elongated rib 75 extends from body half 51a and is received in a corresponding slot (not shown) in body half 51b for alignment and fastening. When the two body portions 51a, 51b are assembled they form a channel or recess 53 to accommodate movement of the belt 72.

The doubling mechanism 50 is mounted within the chassis 224 and engages both the clip advancer 216 and the cam puller bar 222. More specifically, in the embodiment of FIG. 15B, the chassis 224 has a first pair of tabs 225a and a second pair of tabs 225b as shown in FIG. 17A. Lower ferrule 72B is mounted between tabs 225a, 225b. Proximal and distal mounting tabs 54a, 54b fit within slot 222a of cam puller bar 222 to operatively connect doubling mechanism 50 to the cam puller bar 222. Lower ferrule 72b also extends through slot 222a in cam puller 222 for mounting in the lower positioned chassis 224. Lower mounting tab 54b is positioned proximal of tabs 225a. Upper ferrule 72a is positioned within slot 216a of clip advancer 216 of the clip magazine to operatively connect the doubling mechanism 50 to the clip advancer 216. In this manner, the doubling mechanism 50 operably connects the cam puller 222 which effects closure of the jaws 217 (by camming mechanism 220) and the clip advancer 216 which advances clips 214 into the jaws 217.

In the embodiment of FIG. 15A in which the cartridge components are different but the doubling mechanism is the same, the doubling mechanism 50 (of FIGS. 16A and 16B) is mounted to the lower shell 67 via engagement of the lower ferrule 72b within slot 67a for fixation to the lower shell 67. Upper ferrule 72a engages a slot in the clip magazine 63 (or alternatively a clip advancer of the clip magazine) to operatively connect the doubling mechanism 50 to the clip advancer. Lower mounting tabs 54a, 54b are mounted within slot 65a of puller bar 65 to operatively connect the doubling mechanism 50 to the cam puller bar 65 to effect closure of jaws 140 by camming mechanism 138. In this manner, the doubling mechanism 50 operably connects the cam puller bar 65 which effects closure of the jaws 140 by camming mechanism 138 and the clip magazine 63 which advances a clip into the jaws 140.

The operating sequence of the doubling mechanism 50 will now be described in reference to FIGS. 20A-20C which show in cross-section the cartridge components of FIG. 15B which interact with the doubling mechanism 50. FIGS. 20A and 20B show the initial position of the components, which corresponds to the clip applier handle being in the open or at rest position, such as the position of FIG. 15C (or FIG. 1). FIG. 20A shows an exploded view (pre-assembly) and FIGS. 20B and 20C shows the components assembled. Note as assembled, the lower belt fixation member, e.g. lower ferrule 72b, is positioned within tabs 225a, 225b of the chassis 224 and the upper belt fixation member, e.g. ferrule 72b, is engaged within slot 216a of the clip advancer (feeder bar) 216. The lower mounting tabs 52a, 52b fit within slot 222a of the puller bar (puller mechanism) 222. When the handle 228 is actuated (squeezed), e.g., moved toward stationary handle 230, the cam puller 222 is retracted and a doubling of the proximal movement of the clip advancer 216 is effected as shown in FIG. 20C due to the movement of the belt 72. For example, if the cam puller bar 222 is retracted about 0.500 inches, the clip advancer 216 is retracted about 1.000 inches. That is, ferrule 72b in chassis 224 remains stationary, however, as the cam puller bar 222 moves rearwardly (proximally) a first distance with respect to the chassis 224, it induces proximal movement of the body 51 and belt 72 around rounded ends 76a, 76b along the track within body 51, thereby causing the upper fixation member 72a to pull the clip advancer 216 rearwardly a second increased (doubled) distance due to its engagement within slot 216a. After sufficient retraction of the cam puller 222, i.e., near the end of the handle stroke, e.g., with 0.250" remaining in the stroke, the cam puller 222 engages the camming mechanism (cam bar) 220 to retract the camming mechanism 220 to cam the jaws 217 to crimp (close) the clip 214 held within the jaws 217 around the target structure. This delay prior to puller mechanism 222 engaging the camming mechanism 220 is achieved by a slot and pin arrangement whereby the slotted camming mechanism 220 or puller mechanism 222 slides one over the other until it contacts an appropriately spaced stop on the other member resulting in the camming mechanism 220 and puller bar 222 continuing to move (retract in unison) After such retraction, the handle 228 is returned to the initial position, with the puller mechanism 222 moving distally carrying the clip advancer 216 distally and the camming mechanism 220 distally returning to their initial position to move the jaws 217 back to the open position and feed a clip 214 into the jaws 217, the clip advancer 216 traveling twice the return (distal) distance as the cam puller 222, for subsequent squeezing of the handle 228 to apply the next clip. Note that when the engagement point of the camming mechanism 220 has been reached, it is released, allowing the jaws 217 to bias to an open position to receive a clip. The remainder of the stroke allows the clip feeder to advance a fresh clip into the open jaws.

Note the sequence of operation is the same for the embodiment of FIG. 15A, with the handle effecting proximal movement of the cam puller bar 65 which moves the body 51 of the doubling mechanism 50 and the belt 72 to pull back the clip magazine 63 (and clip advancer) an increased, e.g., doubled, distance and retract camming mechanism 138, and release and return of the handle returns the cam puller 65, camming mechanism 138 and clip magazine (and clip advancer) distally to the original position.

An alternate embodiment of the doubling mechanism is shown in FIGS. 21-27B and is designated generally by reference numeral 80. The embodiment of the cartridge mechanism of FIGS. 21-22D is similar in many respects to the embodiment of the cartridge of FIG. 15B and operates in many respects similar to the embodiment of FIGS. 1-14, but includes the doubling mechanism 80. Therefore, for brevity only the doubling mechanism 80 is discussed in detail since the clip applier otherwise operates in a similar manner as the foregoing embodiments. The cartridge components of FIGS. 21-22C include a sleeve tube 256, a cover 258 and chassis 274 which are assembled together and positioned within the sleeve tube 256, thus forming an elongated portion extending from handle 280. Contained within the assembly are a clip magazine 260 containing a line of clips 290, a detent spring 262 to engage and separate the lead clip, a clip floor 264, a jaw mechanism 265 having a pair of jaws 266, a cam or camming mechanism 268 for closing the jaws 266 upon proximal movement, a cam puller rod or puller mechanism 270 for pulling the cam 268 to effect jaw closure, and a toggle lock 272 identical to the toggle lock disclosed in commonly owned co-pending patent publications 2013/0165951 and 2014/0379003, the entire contents of which are incorporated herein by reference. As in the aforedescribed embodiments, cam puller 268 is pulled proximally to close the jaws 266 to effect closure of the clip positioned within the jaws 266 and a clip feeder within clip magazine 260 feeds a clip into the jaws 266. Clip magazine 260 includes a magazine cover 284, a row of clips 290 biased distally by a clip pusher 288 and spring 286, and a magazine base 294 with distal spring 292. The magazine base 294 has a slot 296 (FIG. 22C) to receive a fixation member of the doubling mechanism 80 as described below. The clip applier 250 also has a handle portion 280 having two handle body halves 280a, 280b, anti-backup ratchet 287 with spring 288 and pawl 290, engaging teeth in the rack of ratchet 287, disclosed in application Ser. No. 14/121,344, filed Aug. 22, 2014, the entire contents of which are incorporated herein by reference. Movable handle (trigger) 284 effects jaw closure and clip pusher movement upon movement toward stationary handle 282. The handle 280 is shown in the open position in FIG. 27A and in the closed position in FIG. 27B. Rotation knob 276 can be provided to rotate the elongated portion and/or cartridge to change the position of the jaws. Other handle mechanisms, including those described herein can also be utilized with the doubling mechanism 80. Additionally, the cartridge assembly can be permanently attached to the handle for a single use or alternatively it can be a separable and disposable cartridge, replaceable by another cartridge, for multiple uses in a single procedure. Note the doubling mechanism 80 can also be used with the cartridge mechanisms of FIG. 15A and/or FIG. 15B or with other cartridge mechanisms to achieve its objectives.

Turning now to the doubling mechanism 80 and with reference to FIGS. 23-25B, the doubling mechanism 80 includes a high tensile low friction drive belt 82, a first traveler or carrier 84 and a second traveler or carrier 86. The drive belt 82 loops around rounded supports 87a, 87b of traveler 86 and has two looped ends 82a, 82b each extending into a respective leg 82c, 82d transverse to the longitudinal axis and extending downwardly (as viewed in the orientation of FIG. 23) so the belt 82 can more easily be tightened during manufacture. The legs 82c, 82d can then be trimmed (not shown) for the final assembly.

The traveler 84 has a mounting tab 84a extending upwardly which connects to a slot 260a in clip magazine 260 (FIG. 22D). This operatively connects the doubling mechanism 80 to the clip magazine 260. Note in alternate embodiments the tab 84a can connect to a clip feeder within the magazine 260 where the clip feeder reciprocates within the magazine rather than the entire magazine. Traveler 84 also has a transverse tab 84b (FIG. 25A) with a longitudinal slot formed therein to receive drive belt 82.

As noted above, traveler 84b has proximal and distal rounded ends 87a, 87b around which belt 82 travels, forming a track. Ends 86a, 86b of traveler 86 have a slot for mounting to recesses or slots 270a, 270b of puller rod 270. This operatively connects the doubling mechanism 80 to the cam puller rod (camming mechanism) 270. The puller rod portion 270c between slots 270a, 270b extends through recess 86c in traveler 86. Note that although as shown as a puller rod, a flat plate as in other embodiments disclosed herein could be utilized.

Figure 24:
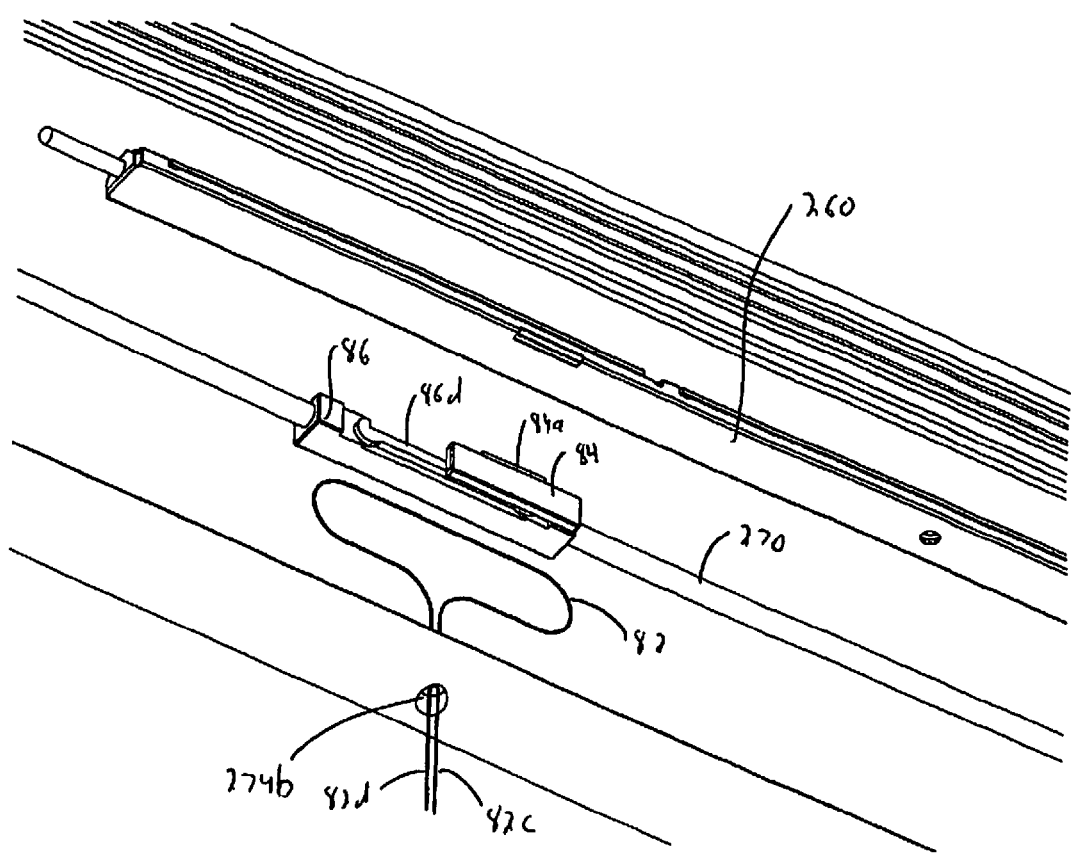
FIG. 24 is an exploded bottom perspective view of certain components of the cartridge mechanism and the stroke doubling mechanism of FIG. 21.
Figure 25A:
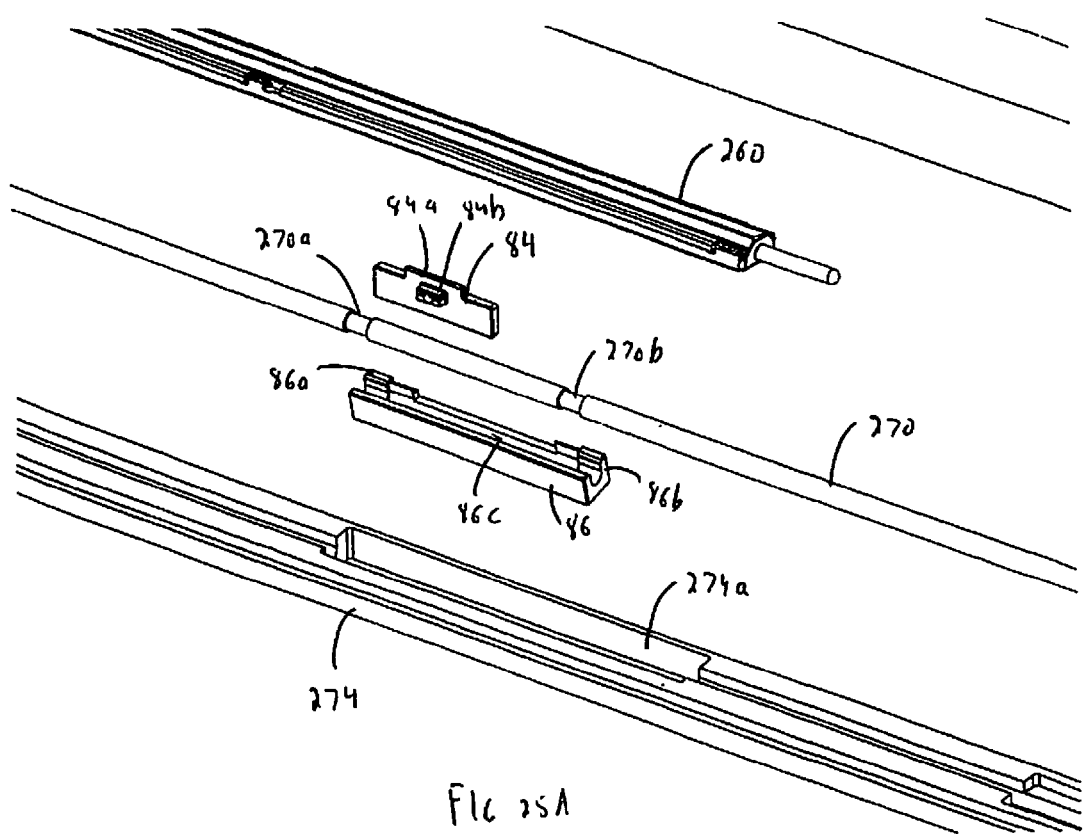
FIG. 25A is an exploded perspective view of certain components of the cartridge assembly and the stroke doubling mechanism, of FIG. 21 viewed from the opposite side of FIG. 23, and the drive belt not shown for clarity.
Figure 25B:
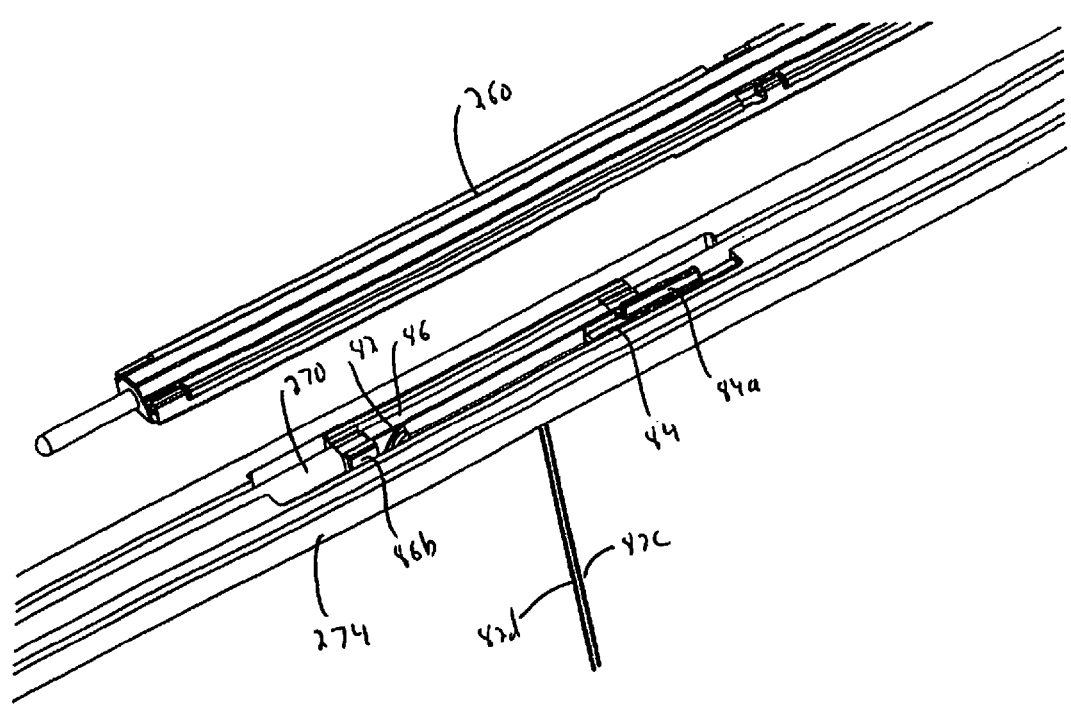
FIG. 25B is a perspective view similar to FIG. 23 showing the stroke doubling mechanism of FIG. 21 mounted in the chassis.
Figure 26:
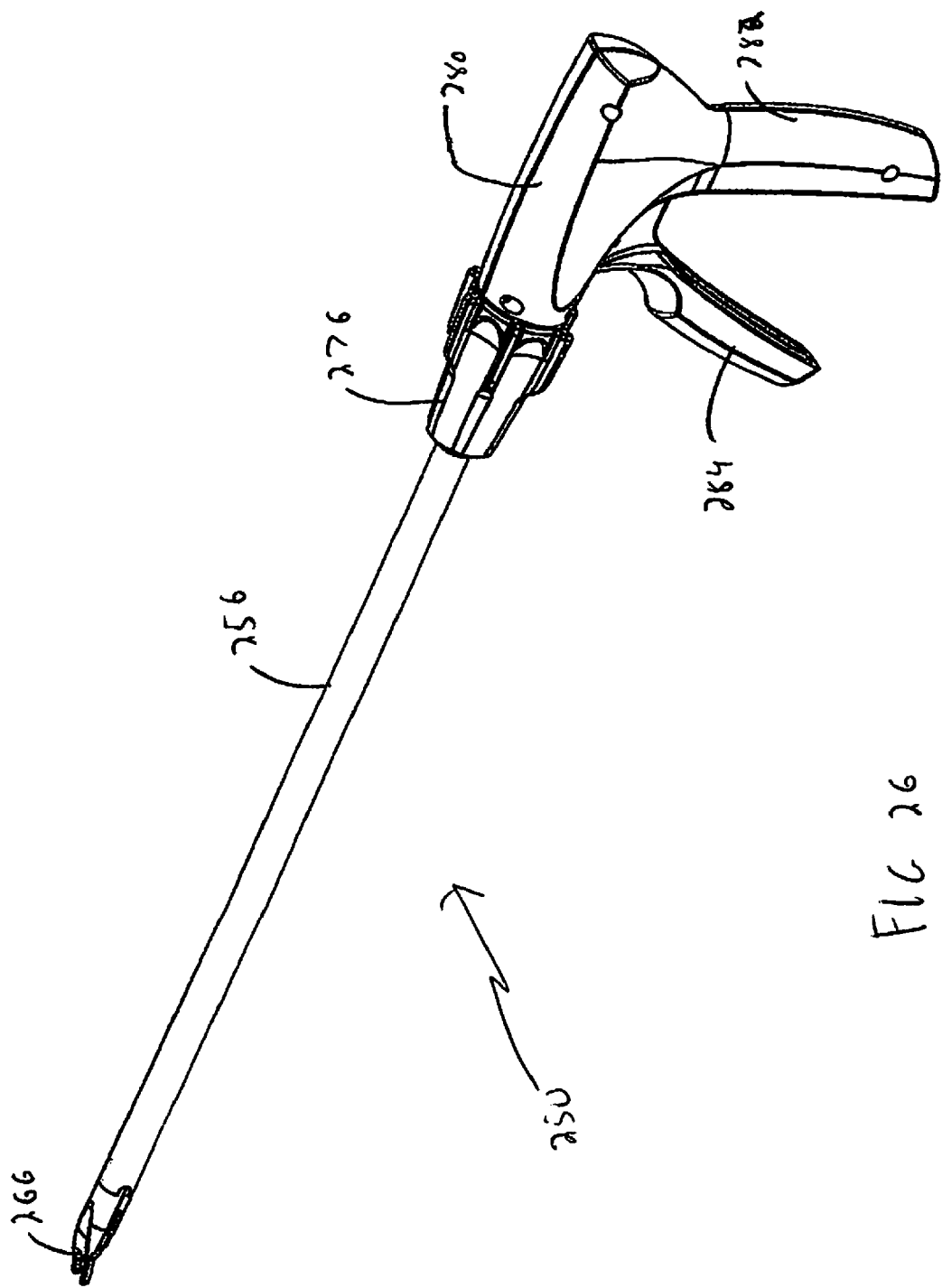
FIG. 26 is a perspective view of the clip applier of FIG. 21.

Travelers 84 and 86 are mounted within a recess 274a in the chassis 274, with traveler 84 alongside a distal region of traveler 86. The legs 82c, 82d of belt 82 can extend through opening 274b in chassis 274 (FIG. 24)

The sequence of operation of the doubling mechanism 80 is similar to that of doubling mechanism in that a drive belt is used to increase, e.g. double, the distance of travel of the clip magazine (and clip feeder) compared to the distance of travel of the cam puller. In use, actuation of the handle 280 by squeezing movable handle (trigger) 284 from the position of FIGS. 26 and 27A retracts the puller rod 270 (mounted within fixed chassis 274) proximally. Due to the engagement of traveler 86 within slots 270a, 270b of the puller rod 270, such movement retracts the traveler 86 and moves the drive belt 82, retracting the traveler 84, thereby pulling the operatively connected clip magazine 260 proximally due to the engagement of tab 84a of traveler 84 within slot 260a of magazine 260. This results in the clip magazine 260 retracting a second distance which is twice the first distance of retraction of the puller rod 270 with each handle stroke. After sufficient retraction of the cam puller (puller mechanism) 270, i.e., near the end of the handle stroke, the puller rod 270 engages camming mechanism 268 to move it proximally as they move back in unison. After such retraction, the handle 280 is returned to the initial position, with the cam puller rod 270, cam 268, and clip magazine 260 returning to their initial position to move the jaws 266 back to the open position and feed a clip into the jaws 266, the clip magazine 260 traveling twice the return (distal) distance as the cam puller rod 270, for subsequent squeezing of the handle 284 to apply the next clip of clip row 290.

Figure 31C:
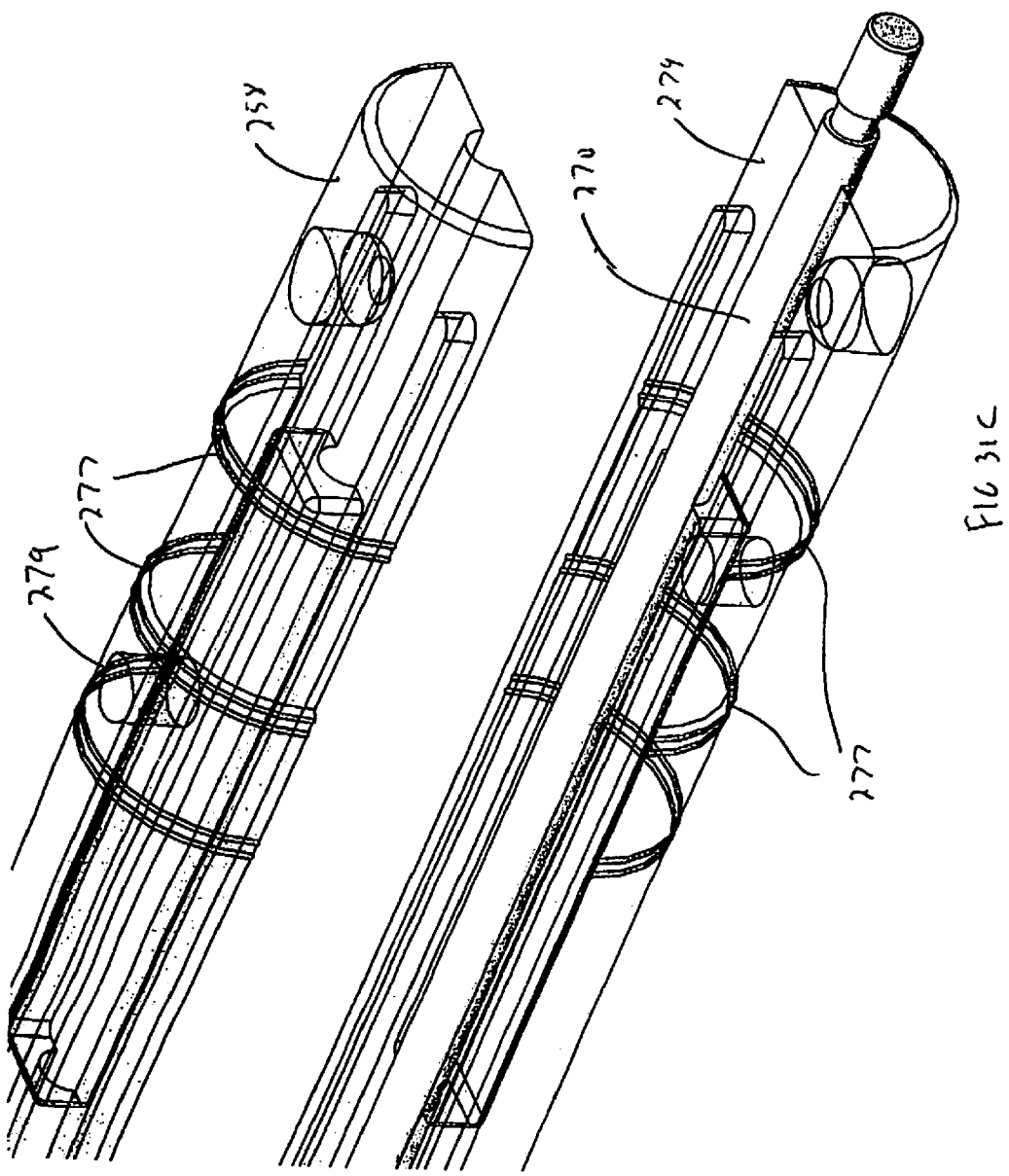

FIGS. 31A to 32 illustrate embodiments of an instrument seal that can be utilized. Such seal can be utilized with any of the embodiments disclosed herein. As noted above, cover 258 and chassis 274 are assembled together, forming an assembly 275, and positioned within a sleeve tube, such as sleeve tube 256 or FIG. 22A. A plurality of annular O-ring seals 277, e.g., three O-rings, are axially spaced along the assembly 275 formed by cover 258 and chassis 274, and sit within the sleeve tube which slides over the assembled cover/chassis, thereby providing a pneumatic seal between the assembly 275 and sleeve tube to prevent leakage of insufflation gas through the clip applier. To provide a seal within the assembly, a viscous sealant is injected through port 279 (or alternatively, multiple ports), in the cover 258 of the assembled unit. The sealing grease exits a second port 279a in the chassis 274 to indicate full capacity. The grease thus fills the body surrounding puller rod 270. The grease also encircles the assembly, filling the groove or reduced diameter portion 279b between O-rings 277. In the alternate embodiment of FIG. 32, the chassis 274 and cover 250, when assembled, form a first sealing grease compartment 281a and a second grease compartment 281b (or alternatively multiple compartments) to surround the reciprocating puller bar 259, thereby preventing passage of gas through the clip applier. When filled to capacity through port 279, the grease overflowing compartment 281a flows to compartment 281b.

FIGS. 27-30 illustrate an embodiment of the stroke increasing and reversing mechanism of the present invention. The clip applier of this embodiment is especially designed for laparoscopic surgery and for insertion through a 5 mm diameter trocar cannula, although it can be utilized with trocar cannulas of other dimensions. The clip applier configuration and components enable insertion through such smaller trocar without sacrificing necessary clip size. It also reduces the risk of formation of a clip or dislodgement of a clip from the jaws during insertion through the trocar cannula. This is all achieved in a reduced cost manner and with a universal handle that can also be used to apply different sized clips. To this effect, the jaws are biased to an open position, inserted without a clip in the jaws, and compressed to a closed position when inserted. Squeezing of the handle advances the distalmost clip into the jaws and the advancer then instantly and biasedly retracts after which continued retraction of the puller retracts the camming mechanism to close the jaws. This action is performed in a single continuous proximal stroke of the handle. This structure has the advantages of insertion without a clip in the jaws and maintaining the jaws in a normal position without a clip (until the handle is activated) so the clip applier can be removed through the trocar before all clips are fired if so desired since there would be no clip in the jaws and the jaws could compress through the trocar cannula during withdrawal.

Figure 28:
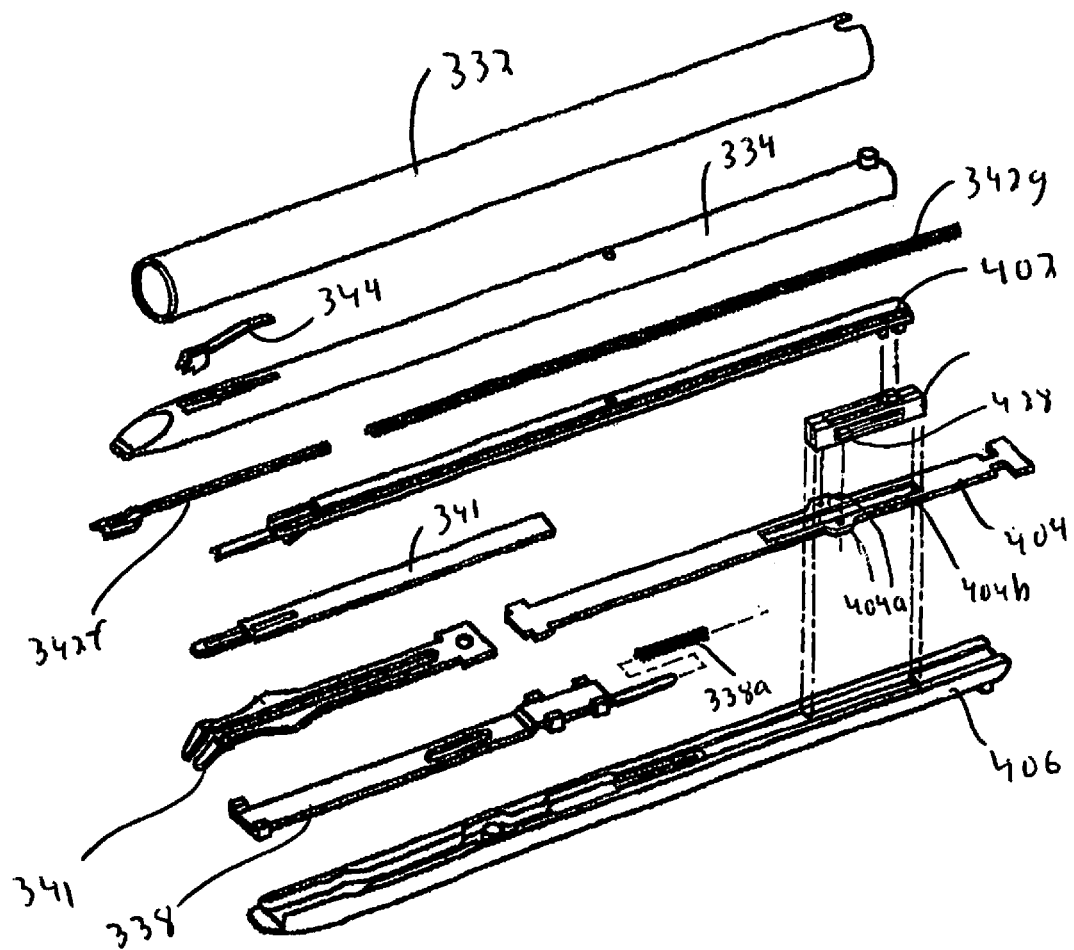
FIG. 28 is an exploded perspective view of the cartridge mechanism components of another embodiment of the present invention having the doubling/reversing mechanism.

The clip applier is similar in many respects the embodiment of FIG. 15A (which is similar to the embodiment of the prior art of FIGS. 1-14), however, it has a doubling/reversing mechanism (assembly). Therefore, for brevity only the differences are discussed in detail. For convenience, like components to clip applier 10 of FIGS. 1-14 have been numbered in FIG. 28 in the "300 series" so that corresponding parts can readily be appreciated. For example, the cartridge components of FIG. 28 include an applicator housing tube 332 identical to tube 32. The housing tube 332 extends distally from a handle portion (similar to the aforedescribed handle portions) to form with other components a distally extending elongated portion. Within the housing tube 332 are a clip detent spring 344 identical to spring 44, an upper shell 334 identical to shell 34, a clip follower 342f and coil spring 342g identical to clip follower 42f and coil spring 42g, respectively, a stationary clip plate 341 identical to clip plate 41, jaws 340 identical to jaws 40 and cam or camming mechanism 338 biased by coil spring 338a identical to cam 38 and spring 38a to close the jaws 340 upon proximal movement. These components are not discussed in more detail herein since their structure and function are identical to the structure and function of these components of FIGS. 1-14. Additionally, other features such as the handle, anti-backup mechanism, etc. are not shown since they are identical to that of FIGS. 1-14 and their description with respect to those Figures is fully applicable to the embodiment of FIG. 15A. FIG. 28 differs from the embodiment of FIG. 1-14 in the provision of the stroke increasing and reversing mechanism 420, also referred to herein as the stroke doubling/increasing assembly. Due to provision of the doubling/reversing mechanism 420, the clip supply magazine 402, puller bar (pulling mechanism) 404 and lower cartridge shell 406 differ from these components of clip applier 10 of FIGS. 1-14 and therefore are not numbered in the "300 series" and are discussed in detail below in conjunction with doubling/reversing assembly 420. The stroke doubling mechanism 420 results in proximal movement of the puller mechanism 404 a distance X effecting a distal movement of the clip feeder (or alternatively a clip magazine) a distance 2X. As noted above, the second distance need not be 2X but can be other multiples of, or increases to, X.

It should be appreciated that the doubling/reversing mechanism 420 can also be used with other cartridge mechanisms such as that shown in FIGS. 15B, 15C and 22A and is shown for use with the cartridge of FIG. 28 by way of example.

Preferably, the mechanism (assembly) effects a doubling of the stroke so the mechanism of this embodiment is also referred to herein as the stroke doubling mechanism. However, it should also be appreciated that other increases in stroke are also contemplated and within the scope of the present invention to achieve the objectives of the present invention.

Figure 29:
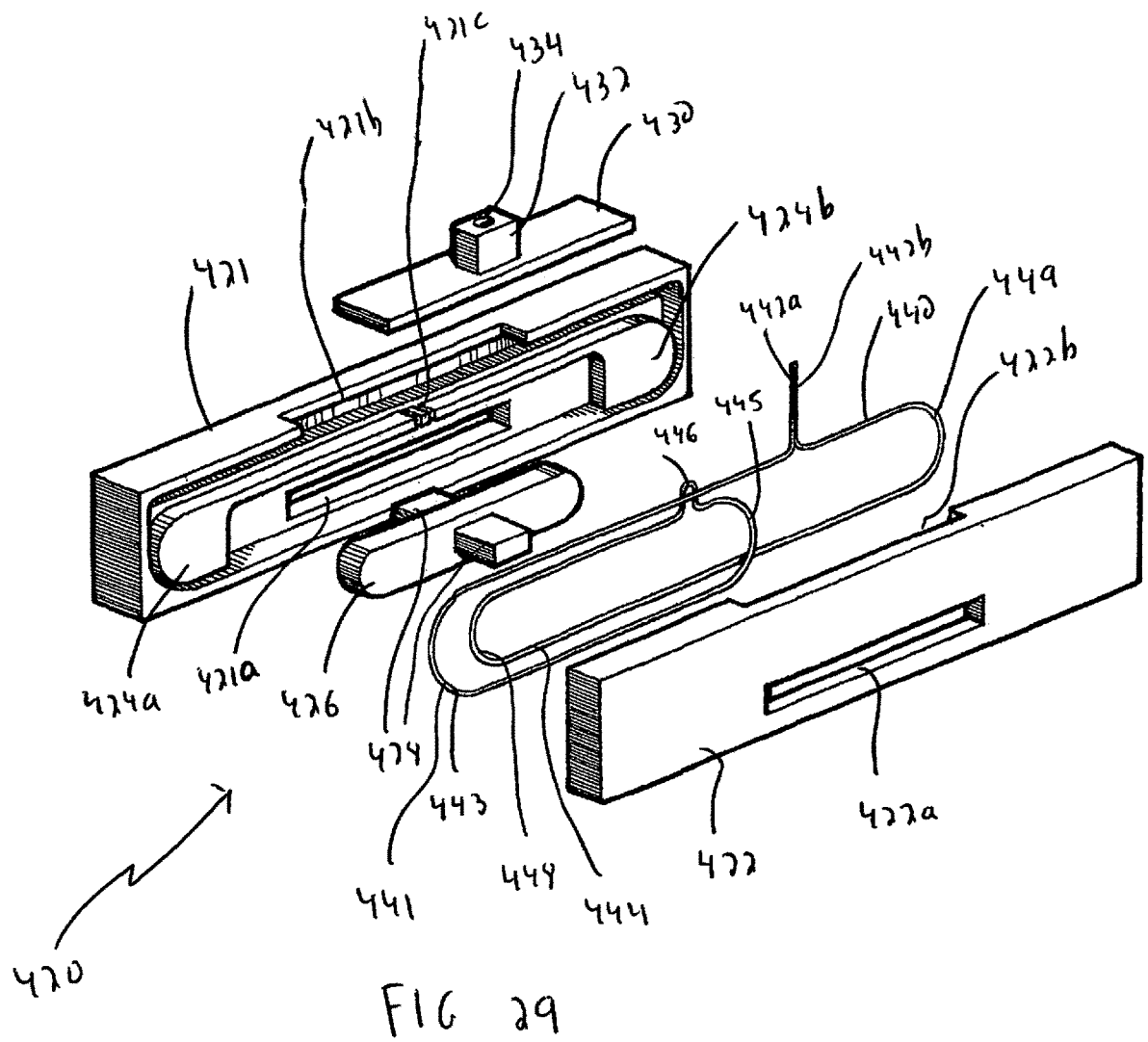
FIG. 29 is an exploded perspective view of the doubling/reversing mechanism of FIG. 28.

Turning now to the doubling/reversing mechanism (assembly) and with reference to FIG. 29, the assembly 420 includes a body composed of a housing 421 and a cover plate 422 connected to housing 421. The housing 421 and cover plate 421 have a recess 421b, 422b, respectively to provide a gap or slot when assembled. The body is fixed within the lower cartridge shell 406 as the traveler 428 moves within the fixed body, and slot 404b accommodates the body. Contained within the housing 421 is a drive belt 440, a first traveler or carrier 426 and a second traveler or carrier 430. The first traveler 426 has a pair of transverse wings or tabs 428 extending therefrom which connect to the puller bar 404 which effects closure of the jaws 341 of jaw mechanism 340 upon sufficient retraction in a proximal direction. Thus, first traveler 426 is operatively connected to the cam puller 404 to provide reciprocating motion of the cam puller 404. Traveler 430 has an upwardly extending tab 432 (as viewed in the orientation of FIG. 29) with an opening 434 to receive the end of the drive belt 440. The traveler 430 is operatively connected to the clip magazine 402 (or clip advancer) to effect movement of the clip advancer 402. Drive belt 440 is preferably a flexible high tensile low friction belt. Drive belt forms a first larger loop 441 and a second smaller loop 444. As seen in FIG. 29, belt 440 can be viewed as starting at leg 442a, extending in a first direction, looping at loop 443 to extend in the opposite (second) direction, then looping back at loop 445, extending upwardly into a fixation point or engagement 446, extending back in the first direction, looping at loop 448 to extend back in the second direction to transition into loop 449 where it loops back in the first direction terminating at leg 442b. Legs 442a, 442b are fixed within tab 432 of traveler 430. Housing 421 has rounded ends 424a, 424b which the larger loop 441 of drive belt 440 extends as it follows the track within housing 421. The shorter loop 444 extends around traveler 426. Housing 421 includes a slot 421a through which one of the wings 428 of traveler 426 extend. The other wing extends through slot 422a in cover plate 422.

The sequence of operation will now be described with reference to FIGS. 30A-30C. In the initial position of FIG. 30A, traveler 430 is engaged with clip advancer (clip feeder bar or mechanism) 402 via engagement of tab 432 with slot 402a of clip advancer 402. Traveler 426 is engaged with cam puller bar (puller mechanism) 404 via attachment of wings 428 with ears 404a of cam puller 404. Note traveler 426 is in a distal position. As discussed above, belt 440 is attached to traveler 430 via securement of legs 442a, 442b within mounting tab 432. Upon squeezing of the handle (proximally), such as the handle 284 or other handles disclosed herein, cam puller bar 404 is retracted proximally (the body remains stationary as it is fixed to lower shell 406), thereby pulling traveler 426 proximally. This causes movement of belt 440 which advances traveler and connected clip feeder 402 distally as shown in FIGS. 30B and 30C which show movement through a complete (full) handle stroke. As can be appreciated, due to belt 440, movement of cam puller bar 404 a first distance A, e.g., about 0.50 inches, effects the reverse (distal) movement of clip feeder 402 a greater second distance B, e.g., about 1.000 inches, thereby effecting a doubling of its movement. Such movement pushes a clip into the jaws 340. When the clip reaches full engagement, a trip mechanism releases the clip advancer to return it to a biased proximal position. The continuation of the proximal handle stroke causes the puller mechanism 404 to engage the camming mechanism 338 to retract the camming mechanism 338 to close jaws 340. This all occurs (clip advancer movement and camming mechanism movement) in a continuous proximal stroke of the handle trigger. When the handle is released, the cam puller 404 returns distally to its initial position of FIG. 30A to move the camming mechanism 338 distally to its initial position; the clip feeder has already returned proximally to its initial position of FIG. 30A (due to the trip mechanism) in preparation for application of the next clip by subsequent squeezing of the handle. Note distal handle release returns the jaws to a clipless state. This enables withdrawal of the clip applier if no more clips are required to be applied. Note that FIG. 30B illustrates an intermediate position for ease of explanation as preferably the handle stroke is a smooth continuous (uninterrupted) stroke to effect movement of the components from the position of FIG. 30A to the position of FIG. 30C. Note also an anti-backup ratchet such as that described above prevents accidental release of the clip from the jaws prior to complete closure of the jaws.

Various changes may be made to the structure embodying the principles of the invention. The foregoing embodiments are set forth in an illustrative and not in a limiting sense. The scope of the invention is defined by the claims appended hereto.

What is claimed is:

1. A laparoscopic surgical clip applier comprising:
a handle at a proximal portion;
an elongated portion extending distally of the handle;
a jaw mechanism at a distal portion, the jaw mechanism including a pair of jaws movable to a closed position to crimp a clip held therein, the jaw mechanism insertable through a trocar cannula without a clip positioned in the jaws;
a puller mechanism operatively connected to the handle;
a camming mechanism operatively connected to the puller mechanism for proximal movement to close the jaws; and
a clip feeder mechanism movable in proximal and distal directions, wherein proximal movement of the camming mechanism to close the jaws effects distal movement of the clip feeder mechanism to feed a clip into the jaws.

2. The clip applier of claim 1, further comprising a stroke increasing mechanism, wherein the stroke increasing mechanism includes a first traveler, a second traveler and a drive belt, wherein movement of the first traveler in a first direction effects movement of the drive belt to move the second traveler in a second direction opposite the first direction, wherein the second traveler is connected to the clip feeder mechanism and the first traveler is connected to the puller mechanism.

3. The clip applier of claim 2, wherein the drive belt has a first loop connected to the first traveler and a second loop movable along a track in a housing of the stroke increasing mechanism.

\* \* \* \* \*